United States Patent
Gertler et al.

(10) Patent No.: US 8,969,292 B2
(45) Date of Patent: Mar. 3, 2015

(54) HIGH AFFINITY LEPTINS AND LEPTIN ANTAGONISTS

(75) Inventors: Arieh Gertler, Rehovot (IL); Eran Elinav, Herzliya (IL); Zamir Halpern, Tel-Aviv (IL)

(73) Assignees: The Medical Research, Infrastructure, and Health Services Fund of the Tel-Aviv Medical Center, Tel Aviv (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 41 days.

(21) Appl. No.: 13/642,669

(22) PCT Filed: Apr. 17, 2011

(86) PCT No.: PCT/IL2011/000322
§ 371 (c)(1),
(2), (4) Date: Feb. 4, 2013

(87) PCT Pub. No.: WO2011/132189
PCT Pub. Date: Oct. 27, 2011

(65) Prior Publication Data
US 2013/0133089 A1 May 23, 2013

Related U.S. Application Data

(60) Provisional application No. 61/326,908, filed on Apr. 22, 2010, provisional application No. 61/379,478, filed on Sep. 2, 2010.

(51) Int. Cl.
*A61K 38/22* (2006.01)
*A61K 38/16* (2006.01)
*C07K 14/575* (2006.01)
*A61K 45/06* (2006.01)
*A61K 38/28* (2006.01)
*A61K 47/48* (2006.01)
*A61K 49/00* (2006.01)
*A61K 31/05* (2006.01)
*A61K 31/575* (2006.01)

(52) U.S. Cl.
CPC ............ *C07K 14/5759* (2013.01); *A61K 38/22* (2013.01); *A61K 38/2264* (2013.01); *A61K 45/06* (2013.01); *A61K 38/28* (2013.01); *A61K 47/48215* (2013.01); *A61K 49/0008* (2013.01); *A61K 31/05* (2013.01); *A61K 31/575* (2013.01); *A01K 2217/00* (2013.01)
USPC .......................................... 514/5.8; 514/21.2

(58) Field of Classification Search
CPC .............. A61K 38/2264; C07K 14/72; C07K 14/5759; C07K 14/47; C07K 14/4703; G01N 2800/044; G01N 33/74
See application file for complete search history.

(56) References Cited

U.S. PATENT DOCUMENTS

2005/0250690 A1 * 11/2005 Gonzalez et al. ............... 514/12

FOREIGN PATENT DOCUMENTS

WO 2006056987 A2 6/2006

OTHER PUBLICATIONS

Hruby, Victor J. Designing Peptide Receptor Agonists and Antagonists. Nature Reviews, 2002. 1:847-858.*
Salomon, Gili et al., "Large-Scale Preparation of Biologically Active Mouse and Rat Leptins and Their L39A/D40A/F41A Muteins Which Act as Potent Antagonists", Protein Expression & Purification, No. 47, pp. 128-136, 2006.
NIV-Spector, Leonora et al., "Indentification of the Hydrophobic Strand in the A-B Loop of Leptin as Major Binding Site III: Implications for Large-Scale Preparation of Potent Recombinant Human and Ovine Leptin Antagonists", Biochemistry Journal, No. 391, pp. 221-230, 2005.
Shpilman, Michal et al., "Development and Characterization of High Affinity Leptins and Leptin Antagonists", The Journal of Biological Chemistry, vol. 256, No. 6, pp. 4429-4442, 2011.

* cited by examiner

*Primary Examiner* — Joseph Woitach
*Assistant Examiner* — Kimberly A Aaron
(74) *Attorney, Agent, or Firm* — Browdy and Neimark, PLLC

(57) ABSTRACT

Leptin muteins, in particular leptin antagonists, with increased binding affinity to leptin receptor are provided. These compounds as well as pharmaceutical composition comprising them are useful for the treatment of any disorder in which a non-desirable or deleterious activity of endogenous leptin or an altered innate immune response is implicated.

15 Claims, 21 Drawing Sheets

SEQUENCE LISTING

```
<160> NUMBER OF SEQ ID NOS: 12

<210> SEQ ID NO 1
<211> LENGTH: 147
<212> TYPE: PRT
<213> ORGANISM: Artificial Sequence
<220> FEATURE:
<223> OTHER INFORMATION: synthetic

<400> SEQUENCE: 1

Ala Val Pro Ile Gln Lys Val Gln Asp Asp Thr Lys Thr Leu Ile Lys
1               5                   10                  15

Thr Ile Val Thr Arg Ile Asn Leu Ile Ser His Thr Gln Ser Val Ser
            20                  25                  30

Ser Lys Gln Lys Val Thr Gly Ala Ala Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Gln Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110
```

```
Gly Val Leu Glu Ala Ser Gly Tyr Ser Thr Glu Val Ala Leu Ser
            115                 120                 125

Arg Leu Gln Gly Ser Leu Gln Asp Met Leu Trp Gln Leu Asp Leu Ser
        130                 135                 140

Pro Gly Cys
145

<210> SEQ ID NO 2
<211> LENGTH: 147
<212> TYPE: PRT
<213> ORGANISM: Homo sapiens

<400> SEQUENCE: 2

Ala Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Gln Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 3
<211> LENGTH: 147
<212> TYPE: PRT
<213> ORGANISM: Artificial Sequence
<220> FEATURE:
<223> OTHER INFORMATION: synthetic

<400> SEQUENCE: 3

Ala Val Pro Ile Gln Lys Val Gln Asp Asp Thr Lys Thr Leu Ile Lys
1               5                   10                  15

Thr Leu Val Thr Arg Ile Asn Leu Ile Ser His Thr Gln Ser Val Ser
            20                  25                  30

Ala Lys Gln Arg Val Thr Gly Ala Ala Ala Ile Pro Gly Leu His Pro
        35                  40                  45

Ile Leu Ser Leu Ser Lys Met Asp Gln Thr Leu Ala Val Tyr Gln Gln
    50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
```

```
           115                 120                 125
Arg Leu Gln Gly Ser Leu Gln Asp Ile Leu Gln Gln Val Asp Leu Ser
        130                 135                 140

Pro Gly Cys
145

<210> SEQ ID NO 4
<211> LENGTH: 464
<212> TYPE: DNA
<213> ORGANISM: Artificial Sequence
<220> FEATURE:
<223> OTHER INFORMATION: synthetic

<400> SEQUENCE: 4
ccatggctgt tccgatccag aaagttcagg atgacaccaa acccctgatc aaaaccatcg        60
ttacccgtat taatctgatc tctcataccc agtctgtttc tgctaagcag cgtgttaccg       120
gcgcggctgc aatcccgggc ctgcatccga tcctgtctct gtctaaaatg gaccagaccc       180 tggctgtttta tcagcaggtt ctgacctctc tgccgtctca gaacgttctg cagatcgcta       240
acgacctgga aaacctgcgt gacctgctgc atctgctggc tttctctaaa tcttgctctc       300
tgccgcagac ctctggcctg cagaaaccgg aatctctgga cggcgttctg gaggcttctc       360
tgtattctac cgaagttgtt gctctgtctc gtctgcaggg ctctctgcag gacatcctgc       420
agcagttgga cgtttctccg gaatgctgat gaaagcttgg atcc                        464

<210> SEQ ID NO 5
<211> LENGTH: 438
<212> TYPE: DNA
<213> ORGANISM: Artificial Sequence
<220> FEATURE:
<223> OTHER INFORMATION: Synthetic

<400> SEQUENCE: 5
gtgcccatcc aaaaagtcca agatgacacc aaaaccctca tcaagacaat tgtcaccagg        60
atcaatgaca tttcacacac gcagtcagtc cctccaaac agaaagtcac tggtgcggct       120
ttcattcctg gctccaccc catcctgacc ttatccaaga tggaccagac actggcagtc       180
taccaacaga tcctcaccag tatgccttcc agaaacgtga tccgaatatc caacgacctg       240
gagaacctcc gggatcttct tcacgtgctg gccttctcta agagctgcca cttgccctgg       300
gccagtggcc tggagacctt ggacagcctg gggggtgtcc tggaagcttc aggctactcc       360
acagaggtgg tggccctgag caggctgcag gggtctctgc aggacatgct gtggcagctg       420
gacctcagcc ctgggtgc                                                    438

<210> SEQ ID NO 6
<211> LENGTH: 438
<212> TYPE: DNA
<213> ORGANISM: Artificial Sequence
<220> FEATURE:
<223> OTHER INFORMATION: Synthetic

<400> SEQUENCE: 6
gtgcccatcc aaaaagtcca agatgacacc aaaaccctca tcaagacaat tgtcaccagg        60
atcaatgaca tttcacacac gcagtcagtc cctccaaac agaaagtcac tggtttggac       120
gccgctcctg gctccaccc catcctgacc ttatccaaga tggaccagac actggcagtc       180
taccaacaga tcctcaccag tatgccttcc agaaacgtga tccgaatatc caacgacctg       240
gagaacctcc gggatcttct tcacgtgctg gccttctcta agagctgcca cttgccctgg       300
```

```
gccagtggcc tggagacctt ggacagcctg gggggtgtcc tggaagcttc aggctactcc    360
acagaggtgg tggccctgag caggctgcag gggtctctgc aggacatgct gtggcagctg    420
gacctcagcc ctgggtgc                                                  438
```

<210> SEQ ID NO 7
<211> LENGTH: 438
<212> TYPE: DNA
<213> ORGANISM: Artificial Sequence
<220> FEATURE:
<223> OTHER INFORMATION: Synthetic

<400> SEQUENCE: 7

```
gtgtcgatcc gcaaggtcca ggatgacacc aaaaccctca tcaagacgat tgtcaccagg    60
atcaatgaca tctcacacac gcagtccgtc tcctccaaac agagggtcac cggtgctgct    120
ttcatccctg ggctccaccc tctcctgagt ttgtccaaga tggaccagac attggcaatc    180
taccaacaga tcctcgccag tctgccttcc agaaatgtga tccaaatatc taatgacctg    240
gagaacctcc gggaccttct ccacctgctg gccgcctcca gagctgccc cttgccgcag    300 gtcagggccc tagagagctt ggagagcctg ggcgtcgtcc tggaagcctc cctctactcc    360
accgaggtgg tggccctgag ccggctacag gggtctctac aggacatgtt gcggcagctg    420
gacctgagtc ccggctgc                                                  438
```

<210> SEQ ID NO 8
<211> LENGTH: 438
<212> TYPE: DNA
<213> ORGANISM: Artificial Sequence
<220> FEATURE:
<223> OTHER INFORMATION: Synthetic

<400> SEQUENCE: 8

```
gtgtcgatcc gcaaggtcca ggatgacacc aaaaccctca tcaagacgat tgtcaccagg    60
atcaatgaca tctcacacac gcagtccgtc tcctccaaac agagggtcac cggtttggac    120
gctgctcctg ggctccaccc tctcctgagt ttgtccaaga tggaccagac attggcaatc    180
taccaacaga tcctcgccag tctgccttcc agaaatgtga tccaaatatc taatgacctg    240
gagaacctcc gggaccttct ccacctgctg gccgcctcca gagctgccc cttgccgcag    300 gtcagggccc tagagagctt ggagagcctg ggcgtcgtcc tggaagcctc cctctactcc    360
accgaggtgg tggccctgag ccggctacag gggtctctac aggacatgtt gcggcagctg    420
gacctgagtc ccggctgc                                                  438
```

<210> SEQ ID NO 9
<211> LENGTH: 438
<212> TYPE: DNA
<213> ORGANISM: Artificial Sequence
<220> FEATURE:
<223> OTHER INFORMATION: Synthetic

<400> SEQUENCE: 9

```
gtgcccatcc aaaaagtcca agatgacacc aaaaccctca tcaagacaat tgtcaccagg    60
atcaatgaca tttcacacac gcagtcagtc tcctccaaac agaaagtcac tggtgcggct    120
gccattcctg ggctccaccc catcctgacc ttatccaaga tggaccagac actggcagtc    180
taccaacaga tcctcaccag tatgccttcc agaaacgtga tccgaatatc caacgacctg    240
gagaacctcc gggatcttct tcacgtgctg gccttctcta gagctgcca cttgccctgg    300
```

```
gccagtggcc tggagacctt ggacagcctg gggggtgtcc tggaagcttc aggctactcc    360
acagaggtgg tggccctgag caggctgcag gggtctctgc aggacatgct gtggcagctg    420
gacctcagcc ctgggtgc                                                  438
```

```
<210> SEQ ID NO 10
<211> LENGTH: 438
<212> TYPE: DNA
<213> ORGANISM: Artificial Sequence
<220> FEATURE:
<223> OTHER INFORMATION: Synthetic

<400> SEQUENCE: 10
gtgtcgatcc gcaaggtcca ggatgacacc aaaaccctca tcaagacgat tgtcaccagg    60
atcaatgaca tctcacacac gcagtccgtc tcctccaaac agagggtcac cggtgctgca    120
gctatccctg ggctccaccc tctcctgagt ttgtccaaga tggaccagac attggcaatc    180
taccaacaga tcctcgccag tctgccttcc agaaatgtga tccaaatatc taatgacctg    240
gagaacctcc gggaccttct ccacctgctg gccgcctcca gagctgccc cttgccgcag    300 gtcagggccc tagagagctt ggagagcctg ggcgtcgtcc tggaagcctc cctctactcc    360
accgaggtgg tggccctgag ccggctacag gggtctctac aggacatgtt gcggcagctg    420
gacctgagtc ccggctgc                                                  438
```

```
<210> SEQ ID NO 11
<211> LENGTH: 438
<212> TYPE: DNA
<213> ORGANISM: Artificial Sequence
<220> FEATURE:
<223> OTHER INFORMATION: Synthetic

<400> SEQUENCE: 11
gtgcccatcc aaaaagtcca agatgacacc aaaaccctca tcaagacaat tgtcaccagg    60
atcaatgaca tttcacacac gcagtcagtc tcctccaaac agaaagtcac tggtgcggct    120
gccgctcctg ggctccaccc catcctgacc ttatccaaga tggaccagac actggcagtc    180
taccaacaga tcctcaccag tatgccttcc agaaacgtga tccgaatatc caacgacctg    240
gagaacctcc gggatcttct tcacgtgctg gccttctcta agagctgcca cttgccctgg    300
gccagtggcc tggagacctt ggacagcctg gggggtgtcc tggaagcttc aggctactcc    360
acagaggtgg tggccctgag caggctgcag gggtctctgc aggacatgct gtggcagctg    420
gacctcagcc ctgggtgc                                                  438
```

```
<210> SEQ ID NO 12
<211> LENGTH: 438
<212> TYPE: DNA
<213> ORGANISM: Artificial Sequence
<220> FEATURE:
<223> OTHER INFORMATION: Synthetic

<400> SEQUENCE: 12
gtgtcgatcc gcaaggtcca ggatgacacc aaaaccctca tcaagacgat tgtcaccagg    60
atcaatgaca tctcacacac gcagtccgtc tcctccaaac agagggtcac cggtgctgct    120
gctgctcctg ggctccaccc tctcctgagt ttgtccaaga tggaccagac attggcaatc    180
taccaacaga tcctcgccag tctgccttcc agaaatgtga tccaaatatc taatgacctg    240
gagaacctcc gggaccttct ccacctgctg gccgcctcca gagctgcccc cttgccgcag    300
```

```
gtcagggccc tagagagctt ggagagcctg ggcgtcgtcc tggaagcctc cctctactcc    360
accgaggtgg tggccctgag ccggctacag gggtctctac aggacatgtt gcggcagctg    420
gacctgagtc ccggctgc                                                  438
```

HIGH AFFINITY LEPTINS AND LEPTIN ANTAGONISTS

TECHNICAL FIELD

The present invention relates to leptin muteins, in particular leptin antagonists, with increased binding affinity to leptin receptor and to pharmaceutical compositions comprising them.

BACKGROUND ART

Obesity is considered a risk for many cancers. Serum leptin levels are often elevated in obese people. Leptin acts as a mitogenic agent in many tissues; therefore, it may act to promote cancer cell growth. In fact, leptin was shown to act as a growth factor for prostate cancer cells in vitro, to induce increased migration of prostate cancer cells and expression of growth factors such as vascular endothelial growth factor (VEGF), transforming growth factor-beta1 (TGF-β1), and basic fibroblast growth factor (bFGF), and to enhance prostate cancer growth. (Somasundar et al., 2004; Frankenberry et al., 2004).

Besides playing an important role in the regulation of food intake and energy consumption in the brain, leptin also acts as a potential growth stimulator in normal and neoplastic breast cancer cells. It was also shown recently to induce cell proliferation in ovarian cancer cells in vitro (Choi et al., 2004).

Leptin has been shown recently to promote T helper 1 (Th1)-cell differentiation and to modulate the onset and progression of autoimmune responses in several animal models of disease (La Cava and Matarese, 2004). If leptin's role is fundamental in Th1-mediated autoimmune diseases or inflammatory diseases, such as inflammatory bowel syndrome, then a therapeutic effect can be anticipated by blocking peripheral leptin action (Matarese et al., 2005). Leptin has also been shown to be involved in the pathogenesis of rheumatoid arthritis and in the development of experimental autoimmune encephalomyelitis (EAE), a mouse model for multiple sclerosis (Peelman et al., 2005).

Consequently, both leptins and leptin antagonists have therapeutic potential. Leptin has in the past been dismissed as a potential drug for treatment of obesity, but recently has been reported to be effective in conjunction with amylin analogs (Turek et. al. 2010) or chemical chaperones (Ozcan et al. 2009). Leptin in conjunction with insulin has similarly been shown to cause improvement in mice with type 1 diabetes (Wang et al. 2010).

International Application PCT/IL2005/001250, herein incorporated by reference in its entirety as if fully disclosed herein, discloses the use of synthetic leptin antagonists in which at least two amino acid residues of the sequence LDFI of the hydrophobic binding site at the positions corresponding to positions 39-42 of the wild-type human leptin are substituted with different amino acid residues such that the site becomes less hydrophobic. The leptin antagonists are useful in treating for example metabolic syndrome, non-alcoholic steatohepatitis, atherosclerosis, type II diabetes, anorexia, cachexia, cancer, auto-inflammatory and autoimmune diseases such as multiple sclerosis, inflammatory bowel syndrome or rheumatoid arthritis.

There is an unmet need to increase the affinity of these leptin antagonists and agonists to their target receptor in order to facilitate efficient treatment at lower doses.

SUMMARY OF INVENTION

We have now found, according to the present invention, that the introduction of certain mutations into a mammalian native leptin, or leptin antagonist as disclosed in WO 2006/056987, increases the binding affinity of the leptin or leptin antagonist to the leptin receptor.

Thus, in one aspect, the present invention relates to a synthetic leptin antagonist consisting of a modified mammalian leptin polypeptide as disclosed in WO 2006/056987 further modified by having the aspartic acid at the position corresponding to position 23 of the wild-type human leptin (D23) substituted with a different amino acid residue that is not negatively charged or having the threonine at the position corresponding to position 12 of the wild-type human leptin (T12) substituted with a different amino acid residue that is hydrophobic; a fragment of said modified mammalian leptin polypeptide, wherein said fragment is itself a leptin antagonist; or a pharmaceutically acceptable salt of the modified mammalian leptin polypeptide or its fragment.

In certain embodiments, D23 is substituted with leucine, and in particular, the synthetic leptin antagonist consists of the amino acid sequence as set forth in SEQ ID NO: 1.

In another aspect, the present invention relates to a synthetic leptin agonist comprising a modified mammalian leptin polypeptide in which D23 is substituted with a different amino acid residue that is not negatively charged or T12 is substituted with a different amino acid residue that is hydrophobic; a fragment of said modified mammalian leptin polypeptide, in which D23 is substituted with a different amino acid residue that is not negatively charged or T12 is substituted with a different amino acid residue that is hydrophobic, wherein said fragment is itself a leptin agonist; or a pharmaceutically acceptable salt of the modified mammalian leptin polypeptide or its fragment.

In yet another aspect, the present invention provides an isolated DNA molecule encoding said leptin antagonist or agonist.

In a further aspect, the present invention provides a pharmaceutical composition comprising said synthetic leptin antagonist or agonist, or a fragment thereof, and a pharmaceutically acceptable carrier.

The pharmaceutical compositions comprising an antagonist may be used in treatment of conditions in which excess leptin or leptin signaling is implicated such as metabolic syndrome, non-alcoholic steatohepatitis, atherosclerosis, type II diabetes, anorexia, cachexia, cancer, or auto-inflammatory and autoimmune diseases such as multiple sclerosis, inflammatory bowel syndrome or rheumatoid arthritis, while the pharmaceutical compositions comprising an agonist may be used in treatment of a disease or condition in which aberrant leptin signaling is implicated, selected from obesity, hyperphagia-related syndromes, type 1 diabetes, metabolic syndrome and atherosclerosis, or in promotion of angiogenesis.

In yet another aspect, the present invention provides a transgenic mouse whose genome comprises a gene comprising a DNA molecule encoding for a synthetic leptin antagonist according to the present invention, or a synthetic leptin antagonist having D23 and T12, which is operably linked to an inducible promoter.

The transgenic mouse of the present invention preferably exhibits insulin resistance and increased levels of blood insulin and blood glucose and may thus be used in a method of screening a substance having therapeutic activity for a disease or disorder selected from the group consisting of hyperglycemia, hyperlipidemia diabetes mellitus type 2 and insulin resistance, the method comprising the steps of: (1) administering a test substance to the transgenic mouse; (2) confirming whether or not said disease or disorder or symptoms of the disease or disorder is suppressed in the transgenic mouse; and (3) selecting the test substance as the substance having therapeutic activity for said disease or disorder when said disease or disorder or symptoms of the disease or disorder is suppressed in the transgenic mouse.

BRIEF DESCRIPTION OF DRAWINGS

FIG. 3A shows the library prior to competition with non-labeled hLBD and FIG. 3B after competition. Yeast cells that were not competed-off were collected for two additional cycles of growth and selection. FL1-H and FL2-H refer to the 2 emission filters used in the flow cytometry experiments (excitation 488 nm).

DETAILED DESCRIPTION OF THE INVENTION

Figure 1:
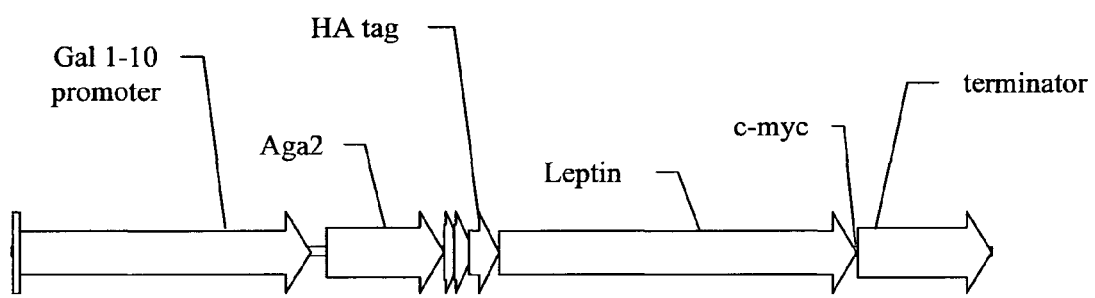
FIG. 1 depicts the schematic structure of the leptin-expressing plasmid in yeast cells. Aga2, Aga2 protein; HA, hemaglutinin.

WO 2006/056987 teaches that the substitution of at least two of the amino acids at the LDFI hydrophobic binding site at positions 39-42 of a wild-type human or non-human mammal leptin sequence with other amino acids such that the site becomes less hydrophobic transforms the wild type leptin agonists to a leptin antagonist. The antagonist has the same affinity toward leptin receptor as the original agonist. To inhibit efficiently leptin action in vivo by using leptin antagonist which has the same affinity toward the leptin receptor as the wild type hormone, a 10-100 fold excess of the antagonist is needed. There are two ways to decrease this high ratio: (1) to prolong the half-life of the antagonists by pegylation; and (2) to increase the affinity of the antagonist toward leptin receptor and subsequently to combine both approaches. The latter approach was implemented in the present application.

In the present work we have used PCR error-prone random mutagenesis of a leptin (agonist) gene followed by selection and identification of the high affinity leptin mutants using yeast surface display methodology, and subsequent preparation of the high affinity mutants as recombinant proteins in Escherichia. coli.

The screening identified high affinity muteins having a single mutation and muteins having multiple mutations. Muteins with increased affinity having few mutations are advantageous over muteins with multiple mutations, because after administration of the mutein to a mammal they are likely to be less immunogenic and thus less likely to induce production of neutralizing antibodies. In the third screen, two high affinity muteins with single mutations were discovered as shown hereinafter: The mutein having the D23 replaced with histidine and the mutein having T12 replaced with isoleucine (see Example 1).

Later, mutations transforming the leptin agonist to a leptin antagonist were introduced to the leptin mutants having high affinity towards leptin receptor. In this way both leptin agonists and leptin antagonists having high affinity towards leptin receptor were produced. As shown below in Example 3, the replacement by rational mutagenesis of D23 with amino acid residues that are not negatively charged resulted in the most potent leptin antagonists.

The leptin agonists of WO 2006/056987 are referred to herein as MLA (mouse leptin antagonist) or HLA (human leptin antagonist), while the improved leptin agonists and antagonists of the present invention are referred to herein by adding the prefix "super active"; thus, for example, improved mouse leptin antagonist is referred to as "SMLA" or super active mouse leptin antagonist and improved human leptin antagonist is referred to herein as "SHLA" or super active human leptin antagonist.

The location of a certain amino acid residue in the proteins or fragments thereof disclosed herein is according to the numbering of the wild type human leptin as depicted in SEQ ID NO: 2 and is designated by referring to the one-letter code of the amino acid residue and its position in the wild type human leptin. Thus, for example, the aspartic acid at the position corresponding to position 23 of the wild-type human leptin, also referred to herein as D23, would be referred to as D23 also in a leptin fragment or in a homologous mammalian leptin of a different size according to alignment algorithms well known in the art of protein chemistry. A substitution of an amino acid residue at a certain position with another amino acid residue is designated by referring to the one-letter code of the amino acid residue, its position as defined above and the one-letter code of the amino acid residue replacing the original amino acid residue. Thus, for example, a substitution of D23 with glycine would be designated D23G.

Figure 10:
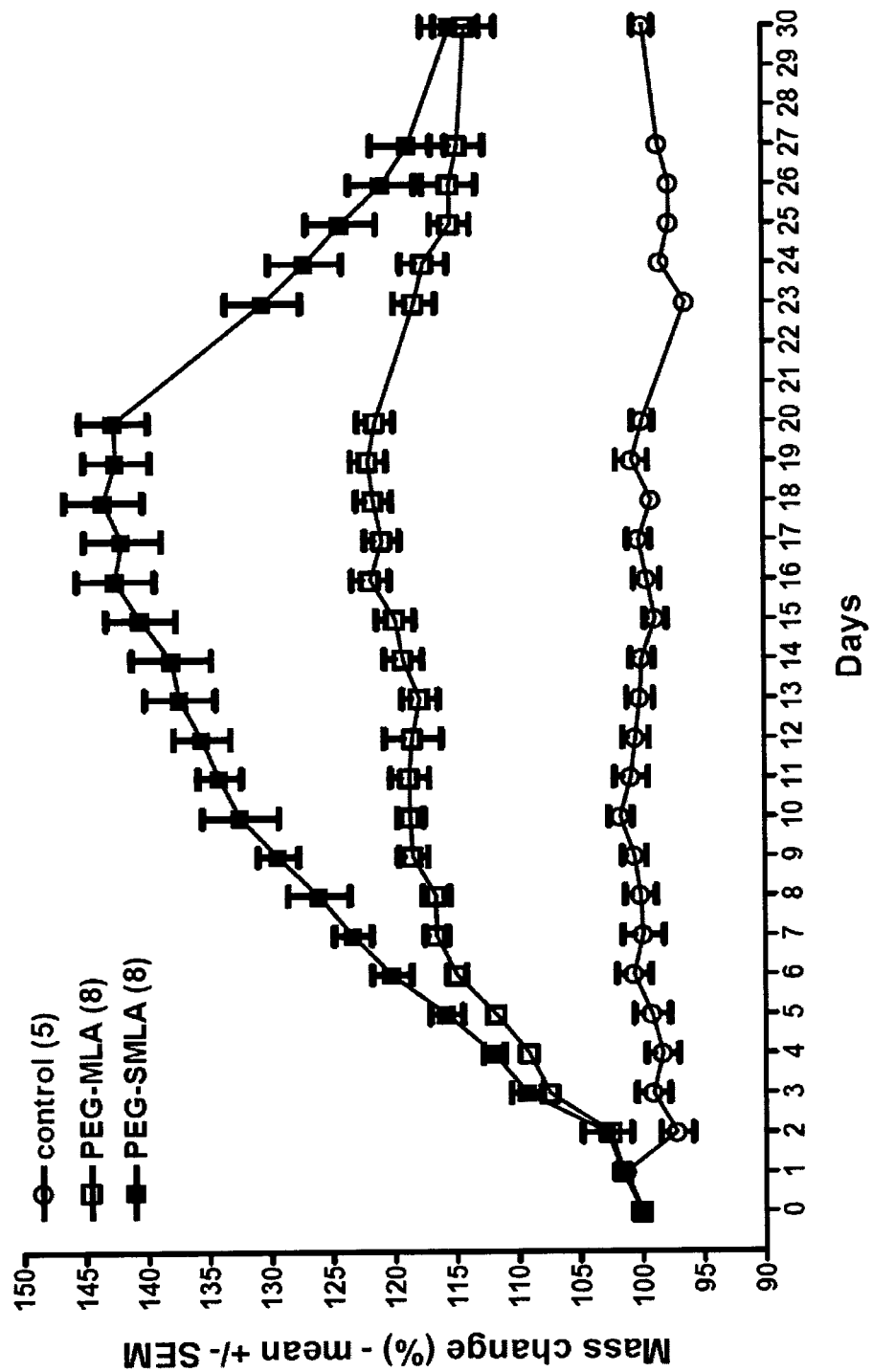
FIG. 10 shows comparison of the effect of PEG-MLA and PEG-SMLA (marked as superANT) on weight gain in mice. Both materials were injected daily at 6.25 mg/kg. After 20 days the injections were ceased and the weight of the mice was checked for another 10 days.
Figure 11:
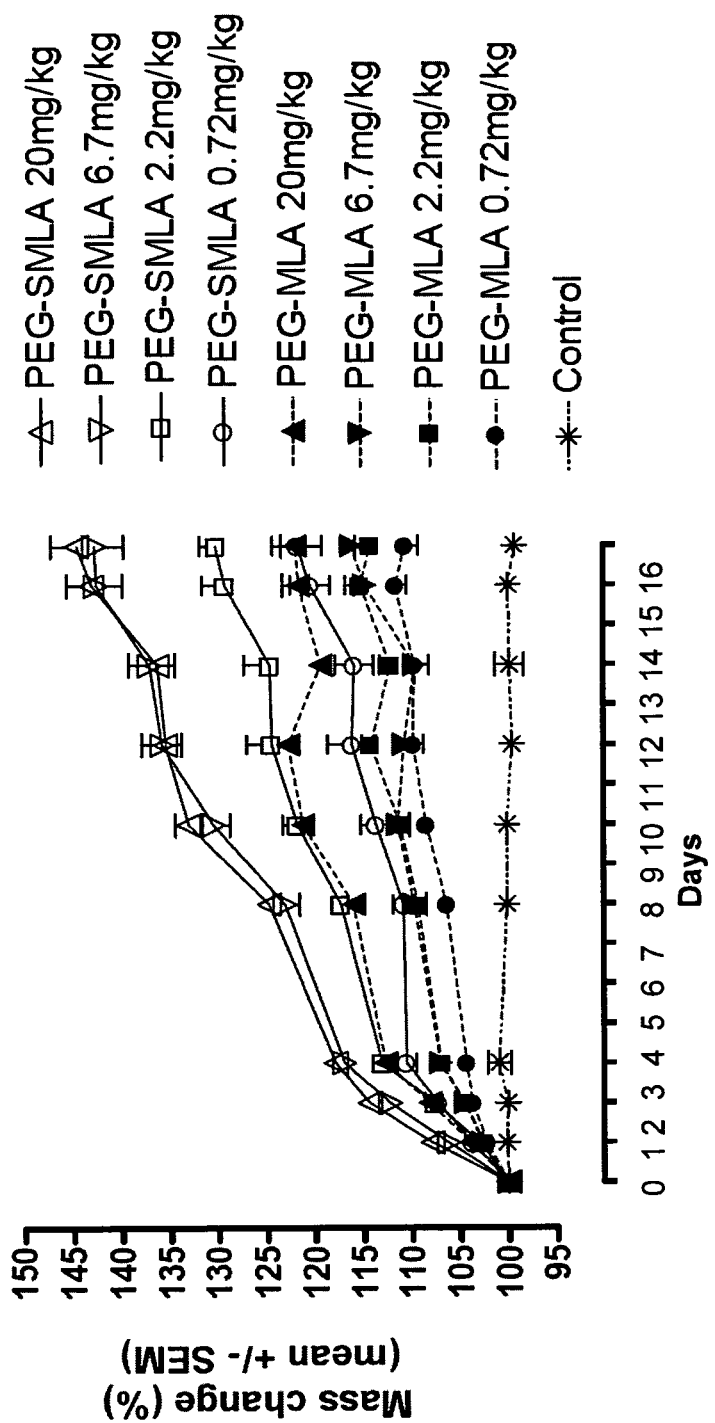
FIG. 11 shows comparison of the effect of PEG-MLA and PEG-SMLA on weight gain in mice in a dose-response experiment. Both materials were injected daily at 20, 6.7, 2.2 and 0.72 mg/kg for a period of 17 days. The results are mean±SEM, n=8.

Though 3-D leptin structure was reported 13 years ago (Zhang et al. 1997) no crystallized complex between leptin and leptin receptor was so far elucidated. Lack of such structure hampers valid structural interpretation of the D23L or other D23 mutations reported in the present application. The suggested interpretation is therefore based on a theoretical complex models reported in the last years (Peelman et al. 2004, Iserentant et al. 2005, Peelman et al. 2006). Those reports suggested that leptin has 3 binding sites that are interacting with leptin receptor. Site I is poorly described and its importance is connected to formation of the putative hexameric complex composed of 2 molecules of leptin reacting with 4 leptin receptors. Binding site II which is a major binding site is found at the surface of helix A and C and it binds to the CRH2 sub-domain of the leptin receptor. This subdomain of human leptin receptor was subcloned in our lab and expressed as a soluble recombinant protein termed leptin binding domain (LBD), capable of forming high affinity 1:1 complex with human or other mammalian leptins (Sandowski et al. 2002). This protein which is also termed CHR2 (cytokine homology region II) was used in the present application as a hook to fish out the high affinity leptin mutants expressed on the surface of the yeast cells as described above. Site III presumably binds to the Ig-like domain of the LR (Peelman et al. 2004, Zabeau et al 2003) and is necessary for activation of the leptin receptor. Using a molecular modeling and mutagenesis approach (Peelman et al. 2004) it was shown that D9, T12, K15, T16 and R20 located on helix A and Q75, N82, D85 and L86 located on Helix C (see FIG. 14) which are structurally close and face the same orientation are most likely involved in interacting with CHR2. Mutations of those residues such as D9S, T12Q, K15S, T16N, R20N, Q75S, N82S, D85S and L86A, L86S, L86N and L86Q significantly lowered the affinity of leptin for CRH2 and affected both binding to CRH2 and the LR signaling. (Peelman et al. 2004, Iserentant et al. 2005). So far no report regarding the putative role of D23 has been published, but the findings according to the present invention (see Table 7) indicate strongly that replacement of D23 by any amino acid not carrying the negative charge was sufficient to increase the affinity toward human Leptin Binding Domain (hLBD; CHR2) and subsequent biological activity. The highest effect was observed with the D23L mutant in binding and cell assays (Table 6 and 7 and FIGS. 7A-D) and confirmed in weight gain in vivo experiments in mice (FIG. 10 and FIG. 11). While the increase in the affinity as determined by binding assays was up to 50 fold, the increases in the in vitro bioassays were only ~13-14 folds, likely because the cells used in those assays have an excess of spare receptors. The increase of potency in in vivo experiment is more difficult to calculate but as shown above it is in a range of 9 to 27 fold. As evidenced, identical D23L mutation in human and ovine leptin antagonists gave similar results. It should be noted that the amino acid sequence of mouse and human sequence in Helix A is identical. Furthermore, D23 is preserved in all mammalian sequences and the amino acid sequences in Helix A are almost identical.

Figure 14:
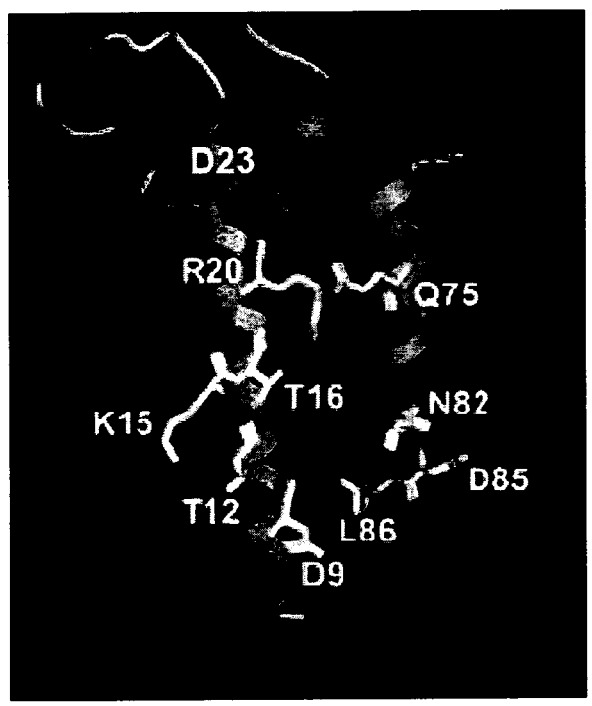
FIG. 14 depicts molecular models of binding site II in mouse leptin. Residues in binding site II that affect binding to CRH2 are colored yellow. Residues in binding site II that affect both binding to the CRH2 sub-domain of leptin receptor and leptin receptor activation are colored orange and D23 is colored green. The T12 residue is part of the binding domain II. From Iserentant et al. (2005).

D23 is located on the C-terminal end of the helix A and is oriented at the same direction like R20, T16, T12 (FIG. 14). Its replacement by non-negatively charged amino acids probably abolishes some not yet identified repulsing effect and therefore increases the interaction with LBD. The increase in the affinity occurred both in the antagonists and agonists mutants, but in contrast to antagonists the biological activity of agonists in in vitro cell based assay was not increased. The reason for such discrepancy is likely related to the fact that the increase in the affinity of SMLA and SHLA origins mainly not from increase of $k_{on}$ but from decrease in $k_{on}$ (not shown) leading to prolonged receptor occupancy. Such prolonged occupancy makes the antagonist more effective but likely does not increase the activity of the agonist. This is similar to the case of human growth hormone whose mutant selected by phage display has also exhibited up to 400-fold increased affinity toward hGH receptor but was not more active in cell bioassay (Lowman and Wells 1993, Pearce et al. 1999).

The present invention thus provides a synthetic leptin antagonist comprising a modified mammalian leptin polypeptide in which: (i) the LDFI hydrophobic binding site at the position corresponding to positions 39-42 or 39-41 of the wild-type human leptin is modified such that from two to four amino acid residues of said hydrophobic binding site are substituted with different amino acid residues such that the site becomes less hydrophobic, said modified mammalian leptin polypeptide being a leptin antagonist; and (ii) the aspartic acid at the position corresponding to position 23 of the wild-type human leptin (D23) is substituted with a different amino acid residue that is not negatively charged or the threonine at the position corresponding to position 12 of the wild-type human leptin (T12) is substituted with a different amino acid residue that is hydrophobic; a fragment of said modified mammalian leptin polypeptide, in which D23 is substituted with a different amino acid residue that is not negatively charged or T12 is substituted with a different amino acid residue that is hydrophobic, wherein said fragment is itself a leptin antagonist; or a pharmaceutically acceptable salt of the modified mammalian leptin polypeptide or its fragment In certain embodiments, D23 is substituted with a hydrophobic or positively charged amino acid residue, wherein the hydrophobic amino acid residue may be leucine, glycine, alanine, tryptophane, histidine or phenylalanine; and the positively charged amino acid residue may be arginine or lysine. In particular, as shown hereinafter in Example 2, in the mutein having the highest affinity towards the leptin receptor among the muteins tested, D23 is substituted with leucine. Therefore, in certain embodiments, D23 is substituted with leucine.

In other embodiments, T12 is substituted with isoleucine.

Muteins with increased affinity towards the leptin receptor as compared with wild type leptin were also identified in which in addition to the substitution of D23 with glycine further mutations had been introduced. For example, in one mutein the amino acid residues at the positions corresponding to positions L68, S97, and S132 in the wild type human leptin had been substituted with other amino acid residues; in another mutein the amino acid residue at the position corresponding to position G112 in the wild type leptin had been replaced with another amino acid residue; and in still another mutein the amino acid residues at the positions corresponding to positions T37 and G44 in the wild type leptin had been substituted with other amino acid residues.

Thus, in certain embodiments, in addition to the substitution of D23 with a hydrophobic or positively charged amino acid residue, further amino acid residues are substituted as follows: (a) the leucine at the position corresponding to position 68 of the wild-type human leptin (L68) is substituted with methionine, the serine at the position corresponding to position 97 of the wild-type human leptin (S97) is substituted with phenylalanine and the serine at the position corresponding to position 132 of the wild-type human leptin (S132) is substituted with tyrosine; (b) the glycine at the position corresponding to position 112 of the wild-type human leptin (G112) is substituted with serine; or (c) the threonine at the position corresponding to position 37 of the wild-type human leptin (T37) is substituted with alanine and the glycine at the position corresponding to position 44 of the wild-type human leptin (G44) is substituted with aspartic acid.

Furthermore, the synthetic leptin antagonist may have at least one substitution, optionally in addition to a substitution of D23, selected from the group consisting of: T121, L68M, S97F, S132Y, G112S, T37A and G44D; and any combination of two or more of these substitutions.

As mentioned above, the substitution of from two to four of the amino acids at the LDFI hydrophobic binding site of a wild-type human or non-human mammal leptin sequence with other amino acids such that the site becomes less hydrophobic transforms the wild type leptin agonists to a leptin antagonist. In certain embodiments, the two to four amino acid residues are substituted with amino acids selected from the group consisting of alanine, arginine, aspartic acid, glutamic acid, glycine, lysine and serine, in particular alanine. In the examples provided hereinafter, the leptin antagonist had three of the four amino acid residues substituted with alanine. Thus, in certain embodiments, three of the four amino acid residues are substituted with alanine; in particular L39A, D40A and F41A.

The leptin antagonist with the highest affinity among those tested had D23 replaced with a leucine. Thus, in certain embodiments, the synthetic leptin antagonist is the mutein in which: (i) the LDFI hydrophobic binding site at the position corresponding to positions 39-42 of the wild-type human leptin is modified such that the leucine at the position corresponding to position 39 of the wild type human leptin is substituted with alanine (D39A); the aspartic acid at the position corresponding to position 40 of the wild-type human leptin is substituted with alanine (D40A); and the phenylalanine at the position corresponding to position 41 of the wild-type human leptin is substituted with alanine (F41A); and (ii) D23 is substituted with leucine (D23L).

In certain embodiments, the human leptin antagonist carrying the mutation D23L has the amino acid sequence as set forth in SEQ ID NO: 1, and the mouse leptin antagonist carrying the mutation D23L has the amino acid sequence as set forth in SEQ ID NO: 3.

As used herein, the term "mammal" includes human mammal as well as non-human mammals. Thus, according to the present invention, the native leptin may be human leptin or a non-human mammal leptin such as, but not limited to, ovine, rat, mouse, horse and pig leptin, and the LDFI sequences represent the 39-42 LDFI sequence of human leptin or of a non-human mammal leptin. In certain embodiments, the leptin is human, mouse or ovine leptin.

As can be seen in Table 6 hereinafter, the affinity to the leptin receptor of the leptin agonists and antagonists identified in the first screening assay range from about 1.5-fold to about 35-fold as compared to wild type mouse leptin. Rational mutagenesis of D23 in leptin antagonists then revealed muteins having a spectrum of affinities toward the leptin receptor ranging from about 18 to about 64 (Table 7). Thus, in certain embodiments, the synthetic leptin antagonist according to the present invention binds to a leptin receptor with an affinity that is up to 100-fold, 90-fold, 80-fold, 70-fold, 50-fold, 30-fold or 20-fold, higher than that of the modified mammalian leptin that is modified only at the LDFI hydrophobic binding site at the position corresponding to positions 39-42 of the wild-type human leptin such that from two to four amino acid residues of said hydrophobic binding site are substituted with different amino acid residues such that the site becomes less hydrophobic.

In a further embodiment, the synthetic leptin antagonist of the invention is in pegylated form and has a variable number of polyethylene glycol (PEG) molecules attached thereto. PEG of molecular weight of about 20 kDa is suitable for this purpose. The pegylation of the leptin antagonists of the invention increases their stability, their plasma half-life and pharmacokinetics.

Also included in the scope of the invention are salts of the modified mammalian leptin polypeptides of the invention. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such salts are preferably used to modify the pharmaceutical properties of the polypeptide insofar as stability, solubility, etc., are concerned.

In another aspect, the present invention relates to an isolated DNA molecule encoding a leptin antagonist of the invention. In certain embodiments, the antagonist has the LDFI hydrophobic binding site at the position corresponding to positions 39-42 of the wild-type human leptin modified by the following replacements: L39A, D40A and F41A and in addition D23 is replaced with leucine. In particular, the DNA molecule comprises a DNA sequence of SEQ ID NO: 4, operably linked to an inducible or constitutively active promoter capable of driving expression of the DNA molecule.

In yet another aspect, the present invention provides a pharmaceutical composition comprising a synthetic leptin antagonist of the invention and a pharmaceutically acceptable carrier, in particular the synthetic leptin antagonist of the amino acid sequence as depicted in SEQ ID NO: 1. In certain embodiments, the pharmaceutical composition comprises a synthetic leptin antagonist in a pegylated form.

Furthermore, it has been found in accordance with the present invention that superactive leptin antagonist administered to mice, in which hepatitis was induced by activation of the innate immune response, provides significant protective effects mediated by inhibition of mononuclear macrophage infiltration into the inflamed organ. Alterations in the innate immune response are considered to be central events in the initial pathogenesis of many auto-inflammatory and metabolic disorders, examples of which include inflammatory bowel disease and non-alcoholic steatohepatitis. The metabolic pathways, such as the leptin pathway, are postulated to interact and modulate the innate immune arm through multiple mechanisms.

Thus, the pharmaceutical composition comprising a synthetic leptin antagonist of the invention is useful in treating any disorder in which a non-desirable or deleterious activity of endogenous leptin or an altered innate immune response, is implicated, as for example in metabolic syndrome, non-alcoholic steatohepatitis, atherosclerosis, type II diabetes, anorexia (by increasing the appetite of the subject suffering from anorexia), cachexia, cancer, auto-inflammatory and autoimmune diseases such as multiple sclerosis, inflammatory bowel syndrome or rheumatoid arthritis.

Thus, in certain embodiments, the invention provides a pharmaceutical composition for treatment of type II diabetes and for the treatment of insulin resistance, especially that associated with obesity in a human or non-human mammal.

In other certain embodiments, the pharmaceutical composition can be used for inhibition of malignant cell growth and can thus be useful in the treatment of cancer such as, but not limited to, breast, colon, ovarian and prostate cancer.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

Methods of administration of the pharmaceutical compositions of the invention include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

In another aspect, the present invention relates to a method for treatment of metabolic syndrome, non-alcoholic steatohepatitis, atherosclerosis, type II diabetes, anorexia, cachexia, cancer, auto-inflammatory and autoimmune diseases such as multiple sclerosis, inflammatory bowel syndrome or rheumatoid arthritis, comprising administering to a patient in need an effective amount of the synthetic leptin antagonist of the invention.

In yet another aspect, the present invention relates to the synthetic leptin antagonist of the invention for use in treatment of metabolic syndrome, non-alcoholic steatohepatitis, atherosclerosis, type II diabetes, anorexia, cachexia, cancer, or auto-inflammatory and autoimmune diseases such as multiple sclerosis, inflammatory bowel syndrome or rheumatoid arthritis.

Besides their potential pharmaceutical use, the leptin antagonists of the invention are useful as research tools for study of the biological activities of the leptin hormone.

The present invention further provides a synthetic leptin agonist consisting of a modified mammalian leptin polypeptide with an intact unmodified LDFI hydrophobic binding site at the position corresponding to positions 39-42 of the wild-type human leptin, wherein the leptin polypeptide has been modified to improve its binding affinity to a leptin receptor as described hereinbefore for the synthetic leptin antagonist. In other words, the present invention provides a synthetic leptin agonist consisting of a modified mammalian leptin polypeptide in which D23 is substituted with a different amino acid residue that is not negatively charged or T12 is substituted with a different amino acid residue that is hydrophobic; a fragment of said modified mammalian leptin polypeptide, in which D23 is substituted with a different amino acid residue that is not negatively charged or T12 is substituted with a different amino acid residue that is hydrophobic, wherein said fragment is itself a leptin agonist, or a pharmaceutically acceptable salt of the modified mammalian leptin polypeptide or its fragment. The particular modifications that improve the affinity for the modified leptin polypeptide towards leptin receptor are selected from the group consisting of D23L, D23G, D23A, D23T, D23H, D23F, D23R, D23K and T12I. Other substitutions may also be introduced into the leptin polypeptide, optionally in addition to the substitutions of D23 and/or T12, such as L68M, S97F, S132Y, G112S, T37A and G44D, and any combination of two or more of these substitutions.

In other aspects, pharmaceutical compositions are provided comprising a pharmaceutically acceptable carrier and the synthetic leptin agonist of the present invention having improved binding affinity to a leptin receptor. So far leptin therapy was used in limited cases in which genetic deficiency of leptin was identified (Bluher et al. 2009) or on a experimental basis in human lipostrophy (Chong et al. 2010). However a continuous effort to utilize leptin as a anti-obesity drug continues and despite the failures a recent report describing successful combination of leptin and amylin therapy was published (Turek et al. 2010). Another report showed that pretreatment of mice with a chemical chaperone such as buphenyl (4-PBA) or tauroursodeoxycholic acid (TUDCA) increased leptin sensitivity (Ozcan et al., 2009).

Also, in light of a recent report showing that in mice with type 1 diabetes treated with leptin in combination with insulin blood sugar fluctuated less, cholesterol levels were lower and there was less body fat deposition than in mice with type 1 diabetes treated with insulin alone (Wang et al., 2010), high affinity leptin agonists may by used in conjunction with insulin or other agents mediating glucose homeostasis in the treatment of type 1 diabetes.

Thus, the pharmaceutical composition may comprise one or more further active agents. For example, for the treatment of diabetes type I, the pharmaceutical composition may comprise insulin in addition to leptin agonist and for the treatment of obesity the pharmaceutical composition may comprise an amylin agonist such as SYMLIN® (pramlintide acetate) or a chemical chaperone such as buphenyl (4-PBA) or tauroursodeoxycholic acid (TUDCA) in addition to the leptin agonist.

In further aspects, the present invention relates to a method for treatment of a disease or condition in which aberrant leptin signaling is implicated, selected from the group consisting of obesity, hyperphagia-related syndromes, type 1 diabetes, metabolic syndrome and atherosclerosis, or in promotion of angiogenesis, comprising administering to a patient in need an effective amount of the synthetic leptin antagonist of the invention.

In certain embodiments, the method is for treatment of obesity and further comprises administering to said patient an amylin analog such as SYMLIN® (pramlintide acetate) or a chemical chaperone such as buphenyl (4-PBA) or taurour-sodeoxycholic acid (TUDCA).

In certain embodiments, the method is for treatment of type 1 diabetes and further comprises administering to said patient insulin.

Similarly, the synthetic leptin agonist of the invention is for use in treatment of a disease or condition in which aberrant leptin signaling is implicated, selected from the group consisting of obesity, hyperphagia-related syndromes, type 1 diabetes, metabolic syndrome and atherosclerosis, or in promotion of angiogenesis. The synthetic leptin agonist may be for use in treatment of obesity in conjunction with administration of an amylin analog or chemical chaperone, or for the treatment of type 1 diabetes in conjunction with administration of insulin.

It has been found in accordance with the present invention that injection of pegylated leptin antagonists (PEG-MLA or PEG-SMLA) induced very strong orexigenic effect, i.e. stimulating effect on the appetite, in both male and female mice, leading to a very fast weight gain originating mainly from fat accumulation (see Examples 4 and 7). This weight gain could be reversed upon ceasing PEG-MLA or PEG-SMLA injections. It was also shown herein that male mice injected with PEG-MLA for an extended period gradually developed insulin resistance and significant difference in insulin level and homeostatic model assessment (HOMA) score compared to the controls (HOMA is a method used to quantify insulin resistance and beta-cell function). A significant increase in blood glucose, blood triglycerides and total cholesterol was also observed—an indication of the appearance of prediabetic metabolic syndrome.

This reversible leptin antagonist-induced obesity, associated with hyperglycemia, hyperlipidemia and insulin resistance, may serve as a fast reversible model of diabetes mellitus type 2 in mice. Such a model can be achieved by injection of PEG-SMLA or by creation of transgenic mice expressing conditionally the DNA sequence encoding the SMLA.

Thus, in another aspect, the present invention provides a transgenic mouse whose genome comprises a gene comprising a DNA molecule encoding for a synthetic leptin antagonist according to the present invention, which is operably linked to an inducible promoter.

In certain embodiments, the DNA molecule encodes a synthetic leptin antagonist consisting of a polypeptide having the amino acid sequence of SEQ ID NO: 1, and preferably is of SEQ ID NO: 4.

As indicated in WO 2006/056987, in order to produce a functional leptin antagonist, at least two of the amino acid residues at positions 39-42 of a wild-type mammal leptin may be substituted with one or more amino acid residues selected from the group consisting of alanine, arginine, aspartic acid, glutamic acid, glycine, lysine and serine. Thus, the genome of the transgenic mouse of the present invention may comprise a gene encoding for these leptin antagonists that in addition have mutations at D23 or T12 as defined herein above.

Of course, also genes encoding for the leptin antagonists of WO 2006/056987 may be introduced into the transgenic mouse. Thus, a leptin antagonist in which any two of the amino acid residues at any of the positions 39-42 of a mammal leptin polypeptide sequence are substituted by alanine, for example at positions 39, 40, or 39, 41, or 39, 42, or 40, 41, or 40, 42, or 41, 42.

In certain embodiments, the isolated DNA molecule encodes a leptin antagonist derived from human leptin. In particular, the DNA molecule is of SEQ ID NO: 5 and encodes the double human leptin mutant L39A/D40A. In another embodiment, the DNA molecule is of SEQ ID NO: 6 and encodes the double human leptin mutant F41A/I42A.

In another embodiment, the isolated DNA molecule encodes a leptin antagonist derived from ovine leptin. In particular, the DNA molecule is of SEQ ID NO: 7 and encodes the double mutant L39A/D40A of ovine leptin. Alternatively, the DNA molecule is of SEQ ID NO: 8 and encodes the double mutant F41A/I42A of ovine leptin.

In another embodiment of the invention, the DNA molecule is of SEQ ID NO: 9 and encodes the triple mutant L39A/D40A/F41A of human leptin. In another embodiment, the DNA molecule is of SEQ ID NO: 10 and encodes the triple mutant L39A/D40A/F41A of ovine leptin.

In still another embodiment, the DNA molecule is of SEQ ID NO: 11 and encodes the quadruple mutant L39A/D40A/F41A/I42A of human leptin.

In a further embodiment, the DNA molecule is of SEQ ID NO: 12 and encodes the quadruple mutant L39A/D40A/F41A/I42A of ovine leptin.

It is important that the promoter controlling the expression of the leptin antagonist gene is inducible, in order to allow spatiotemporal control. For example, it is desirable that the gene be turned on only at the adult stage of development and that it may be turned off after a certain effect has been achieved.

To date, two major systems have been successfully used in transgenic mice, i.e. the tetracycline-inducible system and the Cre/loxP recombinase system (either constitutive or inducible). To use these systems in vivo, it is necessary to generate two sets of transgenic animals. One mouse line expresses an activator (tTA, rtTA, or Cre recombinase) under the control of a selected generic or tissue-specific promoter. Another set of transgenic animals express the "acceptor" construct, in which the expression of the leptin antagonist transgene is under the control of the target sequence for the tTA/rtTA transactivators (or is flanked by loxP sequences). Mating the two strains of mice allows spatiotemporal control of transgene expression.

Other inducible systems have been described, for example promoters comprising synthetic steroid hormone binding domains, and may be used in accordance with the present invention.

Thus, in certain embodiments, the inducible promoter is a tetracycline-controlled transactivator dependent promoter and the transgenic mouse genome further comprises a tetracycline-controlled transactivator. The transactivator may be chosen from two kinds of transactivators; one that enables transcription only in the absence of tetracycline or one that enables transcription only in its presence.

Methods for producing transgenic mice are common knowledge and any appropriate method may be chosen for producing the transgenic mice of the present invention, for example as taught in "Transgenic animal technology: a laboratory handbook, 2nd edition (Carl A. Pinkert, ed., Gulf Professional Publishing, 2002), which is hereby incorporated in its entirety.

As mentioned above, the transgenic mouse of the present invention preferably exhibits insulin resistance and increased levels of blood insulin and blood glucose.

Therefore, in an additional aspect, the present invention provides a method of screening a substance having therapeutic activity for a disease or disorder selected from the group consisting of hyperglycemia, hyperlipidemia diabetes mellitus type 2 and insulin resistance, the method comprising the steps of: (1) administering a test substance to the transgenic mouse; (2) confirming whether or not said disease or disorder is suppressed in the transgenic mouse; and (3) selecting the test substance as the substance having therapeutic activity for said disease or disorder when said disease or disorder is suppressed in the transgenic mouse.

The invention will now be illustrated by the following non-limiting examples:

EXAMPLES

Materials and Methods

Materials—

Recombinant human leptin binding domain (hLBD) (Sandowski et al, 2002), as well as mouse and leptin, and mouse and human leptin antagonists was prepared in our laboratory as described previously (Salomon et al. 2006, Niv-Spector et al. 2005). Synthetic mouse leptin wild type (WT) cDNA optimized for expression in *E. coli* was synthesized by Entelechon Co. Rensberg, Germany (Salomon et al. 2006). Human leptin and mouse interleukin-3 (mIL3) were purchased from Protein Laboratories Rehovot (Rehovot, Israel). Restriction enzymes used in the molecular biology experiments were from Fermentas (Vilnius, Lithuania). Highly pure DNA primers were ordered from Syntezza (Jerusalem, Israel). Lysis buffer, nalidixic acid, 3-(4,5-dimethylthiazol-2-yl)-2,5-diphenyltetrazolium bromide (thiazolyl blue, MTT), puromycin and kanamycin were purchased from Sigma (Sigma, Israel). Superdex 75 HR 10/30, 26/60 and Superdex 200 HR 10/30 columns and Q-Sepharose and SP-Sepharose were from Pharmacia LKB Biotechnology AB (Uppsala, Sweden). Molecular markers for SDS-gel electrophoresis and Bradford protein assay were purchased from Bio-Rad (Bio-Rad, Israel). Bacto-tryptone was from Laboratories Conda (Madrid, Spain). Bacto-yeast extract and Bacto Casamino acids (-Trp, -Ura) were from Difco (Becton Dickinson, Maryland, USA). Sulfo-NHS-LC-Biotin was purchased from Pierce (Rockford, Ill., USA). Plasmid pCT302 and EBY100 strain of the yeast *Saccharomyces cerevisiae* was a kindly gift from Dr. E. T. Boder (from University of Tennessee Knoxville, Tenn., USA). Monoclonal Ab 9e10 was purchased from (Covance, Emeryville, Calif.), FITC-labeled F(ab')2 goat anti-mouse IgG was from (Chemicon) and streptavidin-phycoerythrin (SA-PE) conjugate from (BD PharMingen, San Jose, Calif.). p-STAT-3 (Tyr705) and STAT-3 antibodies were from (Cell Signaling Danvers, Mass., USA) and mPEG-propionyl-ALD 20 kDa was purchased from Jenkem Technology USA Inc. (Allen, Tex.). Fetal bovine serum (FBS), penicillin-streptomycin ('penstrep'; 10,000 units/ml and 10,000 mg/ml) and enhanced chemiluminescence reagent (ECL) were from Biological Industries Ltd. (Beit Haemek, Israel). RPMI-1640 and DMEM medium were from GIBCO (Invitrogen—Carlsbad, Calif.), PelletPaint co-precipitant from (Novagen, EMD Biosciences, Darmstadt, Germany). Luciferase assay reagent was from Promega (Madison, Wis., USA), peroxidase-conjugated Streptavidin was from Jackson Immuno Research Laboratories (West Grove, Pa., USA) and TMB was from Dako (DakoCytomation, Denmark). Other reagents such as Tris, cysteine, arginine, NaOH, HCl, boric acid, Tween 20, ultra pure urea, skim milk were all of analytical grade.

The following kits were purchased: Stratagene GeneMorph® kit, Stratagene QuickChange mutagenesis kit and XL-1 Blue cells (Stratagene—La Jolla, Calif., USA). Qiagen miniprep and Qiaquick Gel extraction kit (Qiagen, Valencia, Calif.). Zymoprep II yeast plasmid miniprep kit (Zymo Research, Orange, Calif.).

The following reagents were prepared in our lab: LB (10 g/L tryptone, 5 g/L yeast extract, 10 g/L NaCl, sterilized), TB (80 g/L tryptone, 160 g/L yeast extract, 33.3 g/L glycerol, sterilized), YPD media (10 g/L yeast extract, 20 g/L peptone, 20 g/L dextrose, sterilized), SD-CAA media (20 g/L dextrose, 6.7 g/L Difco yeast nitrogen base, 5 g/L Bacto casamino acids, 5.4 g/L Na2HPO4 and 8.56 g/L NaH2PO4, sterilized), SG-CAA media (as for SD-CAA, but with 20 g/L galactose instead of dextrose), FACS buffer—PBS buffer (8 g/L NaCl, 0.2 g/L KCl, 1.44 g/L Na2HPO4, 0.24 g/L KH2PO4) adjusted the pH to 7.4, supplemented with 5% bovine serum albumin and 0.05% azide, Lysis buffer for luciferase activity (25 mM Tris-Phosphate, 2 mM DTT, 2 mM CDTA, 10% glycerol, 1% Triton-100, pH 7.8), TN buffer for gel filtration experiments (25 mM Tris-HCl, pH 8 or 9 containing 300 mM NaCl).

Biotinylation of hLBD— hLBD (0.12 mg/ml) was dialysed against PBS (pH 7.5) and incubated with 10-fold molar excess of biotinylation reagent, Sulfo-NHS-LC-Biotin, for 40 min at room temperature. Excess of non reacted biotin was removed by dialyzing against PBS buffer. Biotinylated LBD was capable of forming a 1:1 complex with leptin or leptin antagonists similarly to the non-biotinylated LBD (not shown).

Yeast Surface Display of Mouse Leptin—

Mouse leptin wild type (WT) cDNA was modified by PCR to introduce NheI and BamHI restriction sites at the 5' and 3' ends respectively, enabling subsequent subcloning into acceptor vector pCT302 linearized with NheI and BamHI. The primers used in PCR were 5'-GTACGCAAGC TAGCGCTGTTCCGATCCAGAAAGTTCAGG-3' (SEQ ID NO: 5) to the 5' end and 5'-CGTAGGATCCGCATTCCG-GAGAAACGTCCAACTG-3' (SEQ ID NO: 6) to the 3' end. The PCR product of mouse leptin was digested with NheI and BamHI, extracted, and ligated into linearized pCT302 expression vector. XL-1 Blue cells were transformed with the new plasmid and plated on LB-agar plates containing 100 µg/ml ampicillin Four *E. coli* colonies were isolated and confirmed to contain the mouse leptin cDNA by digestion with NheI and BamHI restriction enzymes. All of the colonies were positive and one of them was sequenced.

Mouse leptin was expressed as an Aga2p protein fusion in the EBY100 strain of the yeast *Saccharomyces cerevisiae* by induction in medium containing galactose (Boder E T, Wittrup K D, 1997.). Hemaglutinin (HA) epitope tag is expressed upstream to the 5' of leptin-encoding DNA, whereas c-myc epitope tag is attached to the 3' of Aga2p-leptin fusion construct, the schematic structure of which is presented in FIG. 1. The c-myc epitope tag can be detected using a mouse mAb 9e10 and a goat anti-mouse antibody conjugated with FITC. Detection of the c-myc epitope tag at the C-terminus of the Aga2p-leptin fusion is indicative of display of the full-length leptin fusion on the yeast cell surface.

Yeast cells transformed with pCT302/mouse leptin wt were grown overnight at 30° C. with shaking in 3 ml of selective glucose medium SD-CAA. After ~18-20 h, Aga1p (a membrane yeast protein)+Aga2p-leptin expression was induced at 30° C. with shaking in 5 ml of selective galactose medium (SG-CAA, where 2% galactose replaces the glucose in SD-CAA). Cultures were harvested after ~20-24 h (1-2 doublings) by centrifugation, washed with PBS containing 5% bovine serum albumin and 0.05% azide (FACS buffer) and incubated for 60 min on ice with anti-c-myc mAb 9e10 (1:100 dilution) and biotinylated-hLBD (final concentration of ~50 nM), washed with PBS and incubated for 30 min on ice with either FITC-labeled F(ab')2 goat anti-mouse IgG (1:50) or a streptavidin-phycoerythrin (SA-PE) conjugate (1:50) or both. Labeled yeast cells were analyzed on a Beckton Dickinson FACSCalibur flow cytometer at the Flow Cytometry Center in the Weizmann Institute.

Construction of the Mouse Leptin Library—

The wild type mouse leptin wt gene was subjected to random mutagenesis using a Stratagene GeneMorph® kit to give a high mutagenesis rate. As described in the study by Raymond et al. (1999), to obtain the best transformation efficiency, homologous recombination primers were designed so that the inserts would have a ~50 bp overlap at each end with the cut acceptor vector. The primer used to make inserts with 5' homology to the cut vector was 5'-GTGGTGGTGGT-TCTGGTGGTGGTGGTTCTGGTGGTGGTG-GTTCTGCTAGCGCTGT TCCGATCCAGAAAGTTC-3', (SEQ ID NO: 7) and the primer used to make inserts with 3' homology to the cut vector was 5'-GATCTCGAGCTATTA-CAAGTCCT CTTCAGAAATAAGCTTTTGTTCGGATC-CGCATTCCGGAGAAACGTCCAACTG-3' (SEQ ID NO: 8). The PCR products were gel-purified and extracted using a Qiaquick gel extraction kit (Qiagen). The PCR product obtained was further amplified using random mutagenesis kit and extracted again. The final PCR product was transformed into the yeast along with linearized pCT-mouse leptin. Homologous recombination in vivo in yeast between the 5' and 3' flanking 50 base pairs of the PCR product with the gapped plasmid resulted in a library of approximately $5 \times 10^5$ mouse leptin variants. 41 µg of mutagenic DNA insert and 8.2 µg of restriction enzyme linearized pCT302 vector backbone were concentrated with Pellet Paint (Novagen) and transformed into EBY100 competent yeast cells (Boder and Wittrup 1997) by 5 electroporations (Meilhoc et al. 1990). A library of $5 \times 10^5$ yeast transformants was obtained, as estimated by plating aliquots of the library and colony counting. The ratio of total insert fragment to cut acceptor vector was maintained at 5:1 for all transformations.

Preparation of Electrocompetent Yeasts for Homologous Recombination—

The method of yeast preparation closely follows that described by Meilhoc et al. (1990). First, 50 ml of YPD was inoculated with the *S. cerevisiae* strain EBY100 (Boder and Wittrup 1997) to an optical density (OD) of 0.1 from an overnight culture of EBY100 in YPD. Next, the cells were grown with shaking at 30° C. to an OD of 1.3 to 1.5 (~6 h of growth). Cells were harvested by centrifugation and suspended in 50 ml cold sterile water. The cells were washed with 25 ml cold sterile water and suspended in 2 ml of ice cold sterile 1M sterile sorbitol. Cells were harvested by centrifugation and suspended in 50 µl 1M sterile sorbitol. Subsequently electroporation of the suspended cells was carried out using a Bio-Rad Gene Pulser with a 0.2 cm cuvette (voltage 1.5 kV, capacitance 25 µF). After pulsing, the cell aliquots immediately resuspended in 1 ml cold 1 M sorbitol and the entire transformation mix was transferred to 50 ml SDC-AA selective media containing kanamycin (25 µg/ml) and penstrep (1:100 dilution) for growth at 30° C. A small aliquot of cells was removed and plated on SDC-AA plates to determine transformation efficiency.

Mouse Leptin Library Screening by Flow Cytometry—

50 ml volume of transformed pool in SD-CAA selective media grown overnight at 30° C. with shaking, diluted to $OD_{600}$=0.05 and grown overnight at 30° C. to $OD_{600}$>1.0. A 5 ml volume of SG-CAA was then inoculated to $OD_{600}$ ~0.5 and grown overnight to $OD_{600}$ of 3-4. Detailed protocols for screening yeast polypeptide libraries have been described (Boder and Wittrup 2000). Briefly, $3 \times 10^8$ induced yeast cells were then labeled with biotinylated hLBD at a concentration of 50 nM for 1 h at 37° C. in FACS buffer. To detect expression of the C-terminal c-myc epitope tag, monoclonal antibody 9e10 (at 1:100 dilution) was added simultaneously in the same incubation. Then yeast cells were washed with ice-cold FACS buffer and resuspended in FACS buffer containing excess of cold non-biotinylated hLBD at a concentration of 2000 nM for 2 h at 37° C. The cells were washed, labeled for one hour with secondary antibodies: streptavidin conjugated with R-phycoerythrin (PE) (1:50) and a goat anti-mouse antibody conjugated with FITC (1:50). Cells were washed and screened by dual-color flow cytometric sorting for yeast on a Beckton Dickinson FACSAria III cell sorter to isolate clones with improved binding to soluble hLBD, relative to wild-type leptin. Collected yeast cells were cultured and induced for expression. Three rounds of sorting by flow cytometry were carried out, with regrowth and reinduction of surface expression between each sort. A total of about $1 \times 10^7$ cells were examined during the first sorting round and ~5% of the population was collected. After a second round of sorting, $1.6 \times 10^5$ cells were collected with 0.5-1% stringency and after the third round of screening, 5000 cells with 0.1% stringency were collected. Each library was frozen and saved at –80° C. according to the protocol (Chao et al. 2006).

DNA Isolation and Sequencing—

After three rounds of sorting, collected cells were plated on selective medium plates to isolate individual clones. DNA from 40 individual clones was extracted using a Zymoprep kit (Zymo Research) according to the manufacturer's protocol. The DNA was amplified by transforming into XL-1 Blue cells (Stratagene). Cells were plated on selective LB plates supplemented with 100 µg/ml ampicillin Colonies from these plates were grown overnight at 37° C. in LB media plus 100 µg/ml ampicillin and DNA was isolated using a Qiagen miniprep kit according to the manufacturer's instructions and DNA was sequenced.

Determination of Affinity Toward Soluble Human Leptin Receptor (hLBD) in Yeast Clones Selected after the Third Screening Cycle—

Individual yeast cells clones after a third screen and wt mouse leptin were grown and induced. $1 \times 10^6$ cells were labeled using biotinylated hLBD at different concentrations (1000, 333, 111, 37, 12, 4, 1.37 nM) along with anti-c-myc Ab and secondary fluorescent Abs as described above. Fluorescence data of c-myc positive yeast were obtained using a Beckton Dickinson FACSCalibur flow cytometer. In order to calculate the dissociation constant $K_d$, the Mean Fluorescence Intensity (MFI), obtained with each of the biotinylated hLBD concentrations tested, was then plotted against the hLBD concentration and using a nonlinear regression (curve fit) with hyperbola equation, analyzed by Prism software (Prisma, GraphPad Prism™ Version 4.0: GraphPAD Software, San Diego, Calif.).

Preparation bacterial expression plasmids encoding mouse leptin muteins—PCR was carried out to introduce NcoI and HindIII restriction sites at the 5'- and 3'-ends respectively, enabling subsequent subcloning of the best mutant mouse leptin binders DNA into pMON3401 vector linearized with NcoI and HindIII. The primers used were AAAAAACCATG-GCTGTTCCGATCCAGAAAG (SEQ ID NO: 9) for the 5' end and AAAAAAAAGCTT TCAGCATTCCG-GAGAAACGTCC (SEQ ID NO: 10) for the 3' end of the leptin mutant. The cDNA of the mouse leptin muteins in pCT302 was digested with NcoI and HindIII, extracted, and ligated into linearized pMon3401 expression vector. *E. coli* MON105 competent cells were transformed with the new expression plasmid and plated on LB-agar plates containing 75 μg/ml spectinomycin for plasmid selection. Four *E. coli* colonies were isolated and confirmed to contain the mouse leptin cDNA by digestion with NcoI/HindIII restriction enzymes. All of the colonies were positive and one of them was sequenced.

Insertion of the L39A/D40A/F41A Mutations into Mouse Leptin Muteins—

The procedure to insert mutations into leptins to create leptin antagonists is disclosed in International Application PCT/IL2005/001250, herein incorporated by reference in its entirety as if fully disclosed herein. To prepare the leptin mutants with antagonistic activity, the pMon3401 expression plasmids encoding the 6 selected mouse leptin muteins (see the section above) were used as starting material. The leptin inserts were modified with the Stratagene QuickChange mutagenesis kit (La Jolla, Calif.) according to manufacturer's instructions, using two complementary primers (Table 1), The primers were designed to contain base changes (marked in bold), to obtain the respective mutations but still conserve the appropriate amino-acid sequence, and to modify a specific restriction site (underlined) for colony screening. The procedure included 18 PCR cycles using Pfu polymerase. The mutated construct was then digested with DpnI restriction enzyme, which is specific to methylated and hemi-methylated DNA (target sequence: 5'-G$^{m6}$ATC-3'), to digest the template and select for mutations containing synthesized DNA. XL-1 competent cells were transformed with the mutated plasmids and grown in 5 ml LB medium and the plasmids were isolated. Five colonies of each mutant were screened for mutation, using the specific designed restriction site, and revealed at least 80% efficiency. Two colonies of each mutant were sequenced and confirmed to contain the mutation but no unwanted misincorporation of nucleotides. Mon105 competent cells were then transformed with the plasmids and used for expression.

Insertion of the D23 Mutants to Plasmid Encoding Mouse Leptin Antagonist—

The D23A, D23G, D23L, D23R, D23K, D23F and D23W mutants were prepared as described in the previous paragraph and the pMon3401 expression plasmids encoding the mouse leptin antagonist (MLA) were used as starting material. The primers details are in Table 1.

Expression, Refolding, and Purification of Mouse Leptin Muteins—

The recombinant mutated mouse leptins with an extra Met-Ala (methionine is cleaved by the bacteria) at the N-terminus were expressed in a 2.5-L culture, upon induction with nalidixic acid, and grown for an additional 4 h. Inclusion bodies (IBs) were then prepared as described previously (Gertler et al. 1998, Salomon et al. 2006) and frozen. Subsequently, inclusion bodies (IBs) obtained from 0.3 L of bacterial culture were solubilized in 50 ml of 4.5 M urea, 40 mM Tris base containing 1 mM cysteine. The pH of the solution was adjusted to 11.3 with NaOH. After 2 h of stirring at 4° C., three volumes of 0.67 M Arg were added to a final concentration of 0.5 M and stirred for an additional 1.5 h. Then, the solution was dialyzed against 10 L of 10 mM Tris-HCl, pH 9, for 60 h, with five or six external solution exchanges. NaCl was added to a final concentration of 100 mM and the protein solution was then applied at maximal flow rate (400-500 ml/h) onto a Q-Sepharose column (5-ml bead volume), pre-equilibrated with the 10 mM Tris-HCl, pH 9, containing 100

TABLE 1

Primers used for the preparation of mouse and human leptin mutants

| Primer | Primer sequence[a] | Modified restriction site[b] | SIN[c] |
|---|---|---|---|
| L39A/D40A/F41 S | 5'-CAGCGTGTTA<u>CCGGCGCGGCTGC</u>CATCCCGGGCCTGC-3' | BshTI (−) | 11 |
| L39A/D40A/F41 A | 5'-GCAGGCCCGGGATGGCAGCCGC<u>GCCGGT</u>AACACGCTG-3' | BshTI (−) | 12 |
| D23G-5 S | 5'-CCATCGTTACCCGT<u>ATT AATG</u>GCATCTCTCATACC C-3' | VspI (+) | 13 |
| D23G-3 A | 5'-GGGTATGAGAGATGC<u>CATTAAT</u>ACGGGTAACGATGG-3' | VspI (+) | 14 |
| D23A-5 S | 5'-CCATCGTTACCCGT<u>ATTAATGCT</u>ATCTCTCATACCCAGTC-3' | VspI (+) | 15 |
| D23A-3 A | 5'-GACTGGGTATGAGAGATAGC<u>ATTAAT</u>ACGGGTAACGATGG-3' | VspI (+) | 16 |
| D23L-5 S | 5'-CCATCGTTACCCGT<u>ATTAATCTG</u>ATCTCTCATACCCAGTC-3' | VspI (+) | 17 |
| D23L-3 A | 5'-GACTGGGTATGAGAGATCAG<u>ATTAAT</u>ACGGGTAACGATGG-3' | VspI (+) | 18 |
| D23R-5 S | 5'-CCATCGTTACCCGT<u>ATTAATCGT</u>ATCTCTCATACCCAGTC-3' | VspI (+) | 19 |
| D23R-3 A | 5'-GACTGGGTATGAGAGATACG<u>ATTAAT</u>ACGGGTAACGATGG-3' | VspI (+) | 20 |
| D23K-5 S | 5'-CCATCGTTACCCGT<u>ATTAATAA</u>GATCTCTCATACCCAG-3' | VspI (+) | 21 |
| D23K-3 A | 5'-CTGGGTATGAGAGATCTT<u>ATTAAT</u>ACGGGTAACGATGG-3' | VspI (+) | 22 |
| D23F-5 S | 5'-CCATCGTTACCCGT<u>ATTAATTT</u>CATCTCTCATACCCAGTC-3' | VspI (+) | 23 |
| D23F-3 A | 5'-GACTGGGTATGAGAGATGAA<u>ATTAAT</u>ACGGGTAACGATGG-3' | VspI (+) | 24 |
| D23W-5 S | 5'-CCATCGTTACCCGT<u>ATTAATTGG</u>ATCTCTCATACCCAGTC-3' | VspI (+) | 25 |
| D23W-3 A | 5'-GACTGGGTATGAGAGATCCA<u>ATTAAT</u>ACGGGTAACGATGG-3' | VspI (+) | 26 |
| T12I-5 S | 5'-GGATGACACCAAAATCC<u>TGATTA</u>AAACCATCGTTACCCG-3' | BclI (−) | 27 |

TABLE 1 -continued

Primers used for the preparation of mouse and human leptin mutants

| Primer | Primer sequence[a] | Modified restriction site[b] | SIN[c] |
|---|---|---|---|
| T12I-3 | A 5'-CGGGTAACGATGGTTT<u>TAATCA</u>GGATTTTGGTGTCATCC-3' | BclI (-) | 28 |
| D23L-5 (human) | S 5'-CAATTGTCACCAGG<u>ATTAATCTG</u>ATTTCACACACGCAG-3' | VspI (+) | 29 |
| D23L-3 (human) | A 5'-CTGCGTGTGTGAAATCAG<u>ATTAAT</u>CCTGGTGACAATTG-3' | VspI (+) | 30 |

[a]S, sense primer; A, antisense primer; all mutations are in bold letters.
[b]Successful mutations were monitored by disappearance (-) or appearance (+) of the respective restriction site (underlined).
[c]SEQ ID NO.

mM NaCl. The breakthrough fraction, which contained the respective leptin mutein, was collected and concentrated to 2-3 mg protein/ml. Then, 18-ml portions were applied to a preparative Superdex 75 column (26/60 cm) pre-equilibrated with 25 mM Tris-HCl, pH 9, containing 300 mM NaCl. Fractions containing the monomeric protein as determined by gel filtration on analytical Superdex 75 HR 10/30 column (1/30 cm) were pooled, dialyzed against NaHCO$_3$ to ensure a 4:1 protein-to-salt ratio and lyophilized.

Preparation of Human Super Leptin Antagonist.

Human leptin antagonist with improved leptin receptor binding was prepared using a similar strategy to that used for preparing the improved mouse leptin antagonists. The primers used were 5'-CAATTGTCACCAGGATTAATCT-GATTTCACACACGCAG (modified restriction site=VspI (+)) (SEQ ID NO: 29) and 3'-CTGCGTGTGTGAAATCA-GATTAATCCTGG TGACAATTG (SEQ ID NO: 30).

Large-Scale Purification of Mouse and Human Leptin D23L/L39A/D40L/F41A Antagonists—

The procedure was essentially described in the previous paragraph with the following changes: IBs obtained from 3 L of bacterial culture were solubilized in 400 ml of 4.5 M urea, 40 mM Tris base containing 1 mM cysteine. The pH of the solution was adjusted to 11.3 with NaOH. After 48 hours of stiffing at 4° C., three volumes of 0.67 M Arg were added to a final concentration of 0.5 M. Then, the solution was dialyzed against 10 L of 10 mM Tris-HCl, pH 9, for 60 h, with five or six external solution exchanges. Prior to application of the protein onto Q-Sepharose column (30-ml bead volume) NaCl was added up to 150 mM. Preparative gel filtration followed by dialysis and lyophilization was conducted as described above. Human leptin super antagonist (D23L/L39A/D40A/F41A) termed SHLA was prepared according to the protocol described previously for human L39A/D40A/F41A (HLA)—(Niv-Spector et al. 2005)

Determination of Purity and Monomer Content—

SDS-PAGE was carried out according to Laemmli (1970) in a 15% polyacrylamide gel under reducing and nonreducing conditions. The gel was stained with Coomassie Brilliant Blue R. Gel-filtration chromatography was performed on a Superdex 75 HR 10/30 column with 0.2-ml aliquots of the Q-Sepharose-column-eluted fraction using TN buffer (25 mM Tris-HCl, 300 mM NaCl, pH 8).

Pegylation of SMLA and SHLA— mPEG-propionyl-ALD 20 kDa was used for pegylation under conditions in which the N-terminal amino group is preferentially pegylated. 150 mg of SMLA or SHLA was dissolved in 111 ml of 0.1 M Na-Acetate buffer (pH 5) and centrifuged at 12000 rpm 10 min to remove the insoluble material. Then 0.2 M of NaBH$_3$CN (2.7 ml) was added and the dissolved protein was conjugated with 1.5 g mPEG-propionyl-ALD 20 kDa that was dissolved in 15 ml of 1 mM HCl. After 20 hours of stirring at 4° C. 160 µl of acetic acid (17 M) was added. The solution was stirred for few seconds, diluted with 1 L ddH$_2$O and applied at maximal flow rate (400-500 ml/h) onto a SP-Sepharose column (20-ml bead volume), pre-equilibrated with 10 mM Na-Acetate, pH 4. The column was then washed with 400 ml of 10 mM Na-Acetate, pH 4 and the pegylated protein was eluted in 10 mM Na-Acetate, pH 5, containing 50 and 75 mM NaCl. Fractions containing the pegylated protein as determined by gel filtration on analytical Superdex 200 column (10/30 cm) were pooled, dialyzed against NaHCO$_3$ to ensure a 2:1 protein-to-salt ratio and lyophilized. Protein concentrations were determined by absorbance at 280 nm using an extinction coefficient (for 0.1% solution of pegylated protein) of 0.200 mg/ml for SMLA and 0.887 for SHLA. Those values apply to the protein part of the pegylated product.

Binding Assay—

Biotinylated mouse leptin served as the ligand in all competitive experiments and the respective mouse leptin or mouse or human leptin antagonist muteins as competitors. The hLBD was used as the receptor source. Polystyrene 96-well microtiter plates were coated overnight at 4° C. with 100 µl of 40 µM hLBD in PBS pH 7.4. Wells were then washed one time with PBST (PBS containing 0.05 Tween 20) and blocked with PBS containing 3% skim milk for two hours in room temperature. All further incubations were carried out at room temperature. Wells were washed one time with PBST and incubated with different concentrations of un-labeled leptins (50 µl/well) for 30 min and then 50 µl of 62.5 µM of biotinylated mouse leptin were added to each well for another two hours. Then the wells were washed three times with PBST and incubated with 1:30,000 streptavidin-HRP in PBS containing 1 Tween 20 for one hour. Subsequently the wells were washed three times with PBST and the reaction was quantified in 450 nm by microplate reader ELISA Plate Reader ELx808—Bio-Tek Instrument Inc. (Winooski, Vt., USA) using TMB according to manufacturer's instructions.

BAF/3 Proliferation Assays—

The proliferation rate of leptin-sensitive BAF/3 cells stably transfected with the long form of hLEPR was used to estimate both agonistic and antagonistic activity of leptins and leptin muteins as described previously (Niv-Spector et al, 2005, Salomon et al. 2006). To determine antagonistic activity, 0.05 ng WT homologous leptin was added to each well, which also contained different concentrations of muteins. The average absorbance in wells without leptin (negative control) was used as a blank value and subtracted from other absorbance values to yield the corrected absorbance values. The average absorbance in wells with WT leptin after subtracting the negative control was used as a positive control to calculate percent inhibition. The inhibition curves were drawn using the Prisma (4.0) nonlinear regression sigmoidal one-site competition program (Prisma, GraphPad Prism™ Version 4.0; GraphPAD Software, San Diego, Calif., U.S.A.) and the $IC_{50}$ values were calculated. It should be pointed out that all mammalian leptins are capable of activating human leptin receptor to almost identical degree (Gertler et al. 1998, Raver et al. 2000, Niv-Spector 2005).

Determination of Biological Activity by Activating Luciferase Reporter Gene—

H-49 cells line, received from Dr. M. Einat (ARO, Israel), are HEK-293 cells stably transfected with three constructs: phOB-Rb (long form of human leptin receptor), pAH32 (luciferase reporter construct) and pgkPuro (expression vector containing the puromycin resistance gene) at a ratio of 4:4:1 as described previously (Gertler et al. 2007). H-49 cells were briefly dissociated with trypsin and resuspended in DMEM supplemented with 10% FCS, 50 μg/ml streptomycin, 50 units/ml penicillin and 2 μg/ml puromycin. Resuspended cells were plated in 24-well tissue-culture plates at $5 \times 10^5$ cells per well in a final volume of 500 μl. After 16 h, the medium in each well was replaced with 300 μl DMEM. Mouse leptin mutants were added at different concentrations with constant concentration of WT mouse leptin. The dilutions were made in DMEM supplemented with 0.5% BSA. Three replicates were used for each concentration and a triplicate without leptin served as negative controls. After 18 h of incubation at 37° C. ($CO_2/O_2$ 5:95), the cells were harvested with 100 μl lysis buffer and frozen at −80° C. Each cell lysate (50 μl) was mixed with Promega luciferase assay reagent and luciferase activity was determined. The measured luminescence was normalized to the amount of protein in each well. Protein concentration was measured by Bradford assay according to the manufacturer's protocol (Bio-Rad, Israel). The results were analyzed by Prizm software, according to a nonlinear regression one site competition curve.

STAT-3 Phosphorylation Inhibition—

CHO cells stably expressing the long form of mouse leptin receptor (ObRb) were grown to 80% of confluence in 24-well plates and then in serum deprived medium for 16 h before stimulation with hormones. Then cells were incubated in serum-free medium in the presence or absence of various concentrations (0.2-12.8 ug/ml) of mouse leptin mutant and one concentration of mouse leptin WT (0.1 μg/ml) for 20 min in 0.5 ml in 24 wells plate. Following these treatments, cells were harvested in 75 μl of ice-cold lysis buffer. Lysates were clarified by centrifugation at 12000 rpm for 10 min and supernatants kept for Western blot analyses. Protein concentrations of supernatants were determined using the Bradford assay. Cell proteins (20 μg) were resolved in SDS-PAGE followed by Western blot using p-STAT-3 (Tyr705) (cat #9138) and STAT-3 (cat #9132) antibodies. Then, Western blot bands were revealed by enhanced chemiluminescence (ECL).

In Vivo Experiments—

Female C57Bl mice were intraperitoneally administered with pegylated mouse or human leptin antagonist (PEG-MLA or PEG-HLA) or superactive PEG-MLA (PEG-SMLA) or human superactive PEG-HLA (PEG-SHLA) at 6.25 mg/kg/day for a period of 20 days. In this period, food intake and weight gain were recorded daily and averaged for a period of 7 days. At day 20, 3 mice of each group were sacrificed and fat content, liver enzymes and lymphocyte subpopulations were measured. In the weaning part of the experiment, the treatment was ceased after 20 days and reversibility of the leptin deficiency phenotype was recorded.

The second experiment was carried out in a similar manner using 4 doses of either PEG-MLA or PEG-SMLA: 20, 6.7, 2.2 and 0.72 mg/kg/day and lasted 17 days. In all experiments animals were maintained under 12-h light-dark cycles, in accordance with regulations of the institutional animal and care authority of the Tel Aviv Sourasky Medical Center.

Example 1

Screening for Leptin Mutants with Improved Binding to Soluble Human Leptin Receptor (i) Functional Expression of Leptin on the Surface of Yeast Cells.

Figure 2A:
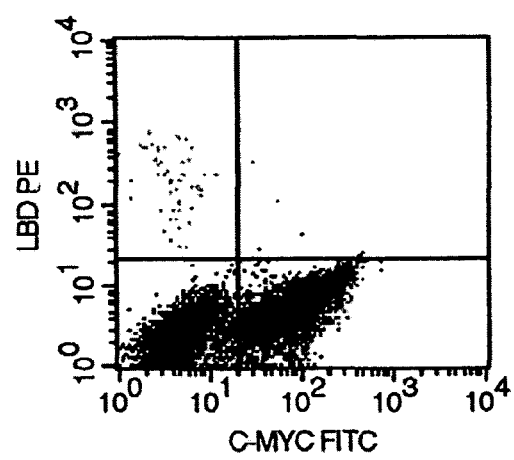
FIGS. 2A-C show flow cytometry analysis of yeast surface display of mouse leptin. The c-myc epitope tag was detected using the mouse monoclonal antibody 9e10 and a goat anti-mouse antibody conjugated with FITC (A), the expressed leptin was detected using biotinylated soluble human leptin receptor (hLBD) and streptavidin-phycoerythrin (SA-PE) conjugate (B) and the two labels could be detected simultaneously using the FACSARIA flow cytometery system (C).
Figure 2B:
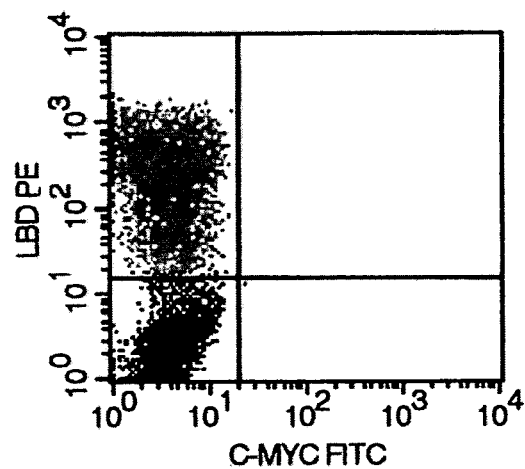
Figure 2C:
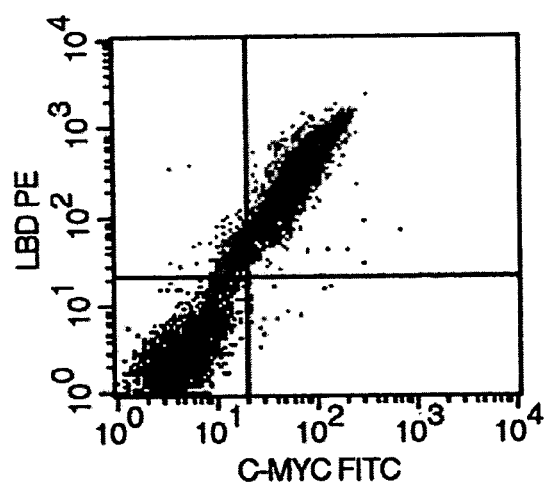

Mouse leptin was expressed on the surface of yeast cells as a fusion to the Aga2p agglutinin subunit, on the surface of yeast (Boder and Wittrup K D, 1997). Expression of the Aga2p+leptin fusion on the surface of yeast was measured by immunofluorescent labeling of the c-myc epitope tag attached to the C-terminus of the Aga2p+leptin fusion by flow cytometry, indicating in frame expression of c-myc (FIG. 2A). The presence of the c-myc tag indicates that the full-length leptin fusion capable of interacting with biotinylated hLBD is displayed on the yeast cell surface. (FIG. 2B), whereas negative control yeast displaying an irrelevant EGFR, did not show any signal (not shown). Furthermore, two color labeling demonstrated a tight correlation of hLBD binding with c-myc epitope display (FIG. 2C).

TABLE 2

Sequence changes in 40 clones selected after 3 screening cycles

| Clone number* | Sequence change** |
|---|---|
| H1, H23 | S25F, L49M |
| H2 | A125T, S132Y |
| H3, H4, H5, H8, H9, H11, H13, H15, H21, H26, H31, H35, L2 | D23G, L68M, S97F, S132Y |
| H6, | D23G, V30D, Y119H |
| H7, H18, H27, H33 | K11R, Q34R, T37A, F92C, S97Y, I136V |
| H12, H20, H24, H25, H28, H29, H32, H36, H37, H38, H39, H40 | S97Y |
| H16 | D23G, G112S, |
| H17 | S109F |
| H22 | T12I |
| H30 | D23H |
| H34 | No change |
| L1 | D23N, Q34L, L114P |

*H- for higher stringency clones, L- for lower stringency clones. Some of the clones were sequenced with cmyc primer, so the end of C- terminal sequence (12 last amino acids in helix D of leptin) was not sequenced.
**The most frequent mutations change (D23) that was found in 18 clones was (ii) Screening the Leptin Library to Select Clones with Improved Binding to hLBD.

Figure 3A:
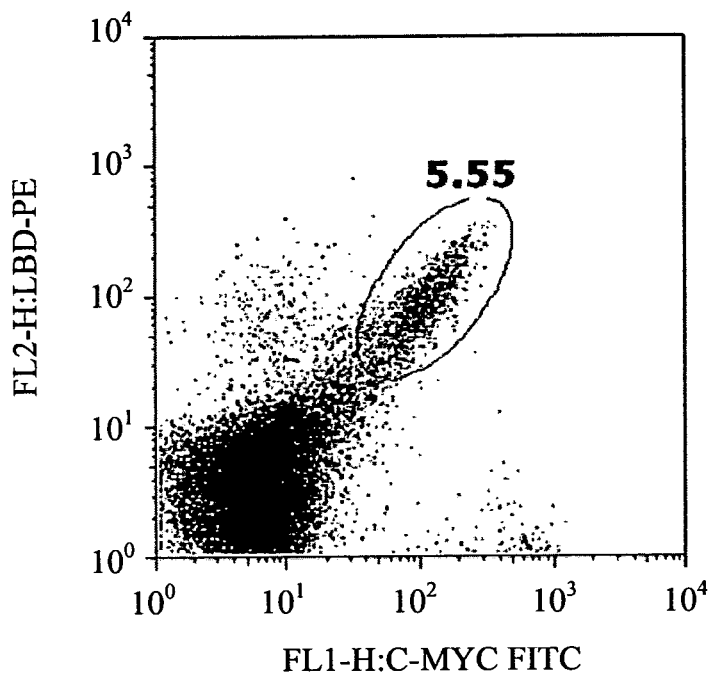
FIGS. 3A-B show representative figures from one of the sorting experiments.
Figure 3B:
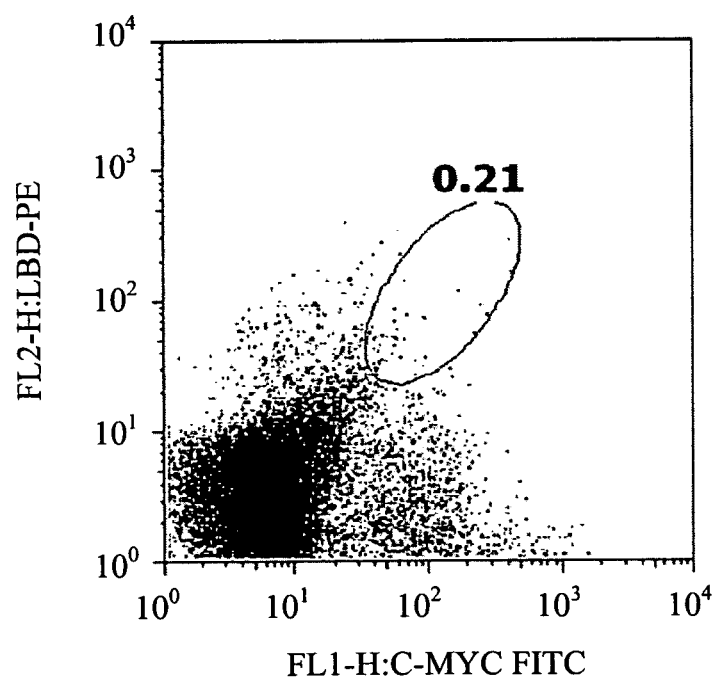

A yeast-displayed library of leptin mutants with a diversity of $5 \times 10^5$ clones was constructed using a Stratagene GeneMorph® random mutagenesis kit. This library was screened through three rounds of sorting by flow cytometry, with re-growth and re-induction of surface expression between each cycle of sorting, to isolate clones with improved binding to hLBD. The yeast library was screened by dual-color flow cytometry for clones that both displayed leptin (as determined by indirect immunofluorescence of a C-terminal c-myc epitope tag), and bound to biotinylated hLBD. The screening approach used kinetic binding screen, by labeling yeast to saturation with fluorescently labeled hLBD followed by incubation in the presence of excess non fluorescent hLBD competitor. Labeled wild type control cultures were prepared in each cycle of sorting for assistance in setting sort windows and confirmation of progress in library enrichment. Cells that exhibited fluorescence after being competed-off by non biotinylated hLBD were collected for re-growth (see FIG. 3, right panel). Forty mutants obtained in the third selection cycle were sequenced (Table 2) resulting in identifications of 13 new distinct sequences, with total of 23 amino acid changes, ranging from a change of 1 to 6 amino acids (Table 2). The most frequent mutation that occurred in 18 out of 40 clones was exchange of D23 to G, to H or N.

(iii) Affinity Determination Using Equilibrium Binding Titration Curves.

Figure 4A:
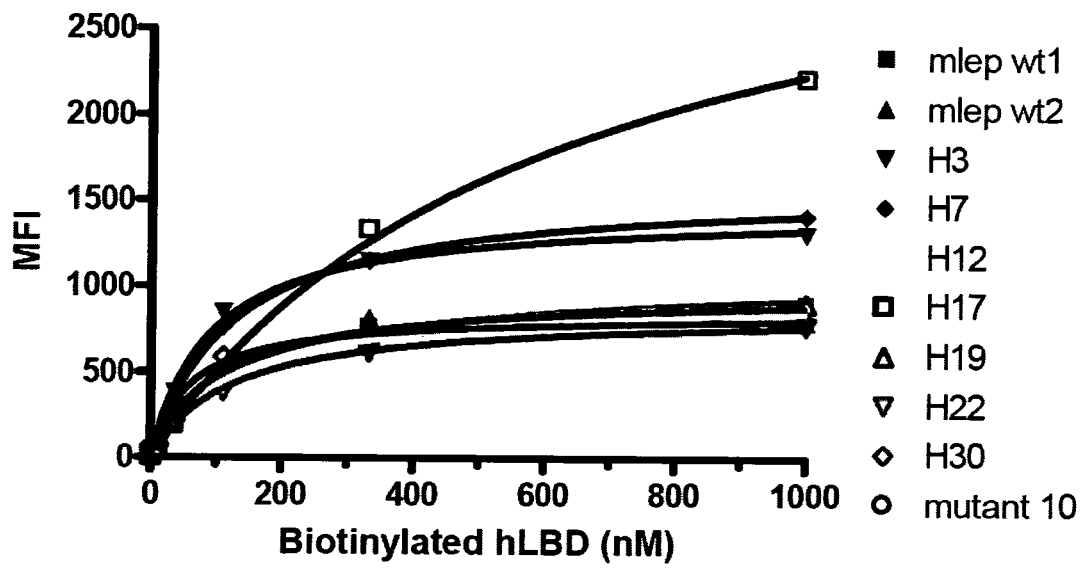
FIGS. 4A-B depict determination of affinity toward soluble human leptin receptor (hLBD) in 13 yeast clones selected after the third screening cycle. MFI, mean fluorescent intensity; mlep wt, mouse wild type leptin.
Figure 4B:
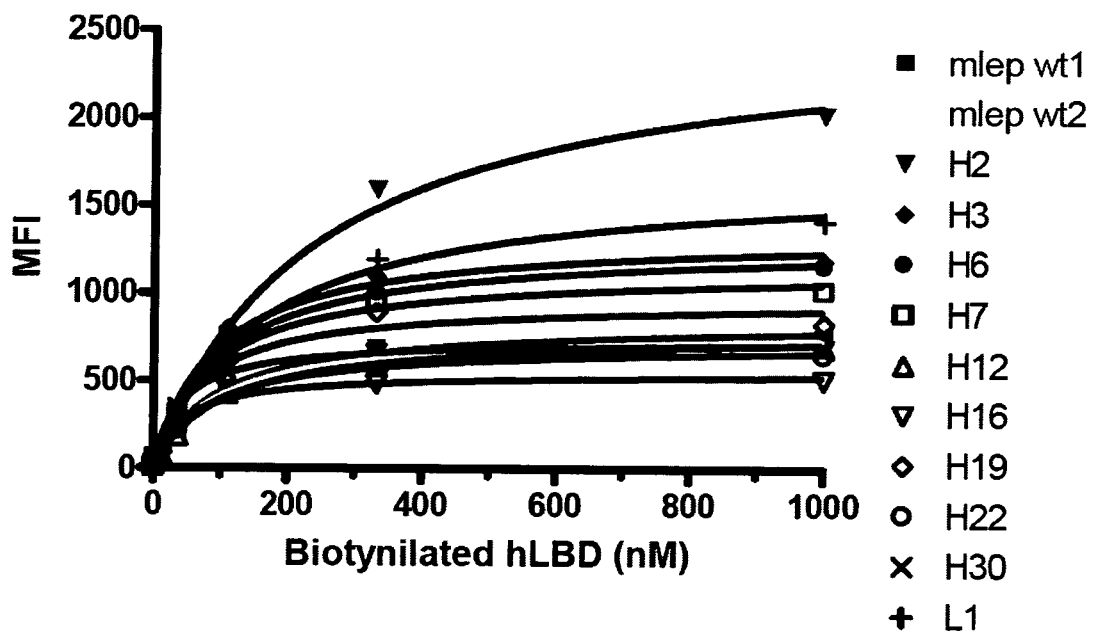
Figure 5A:
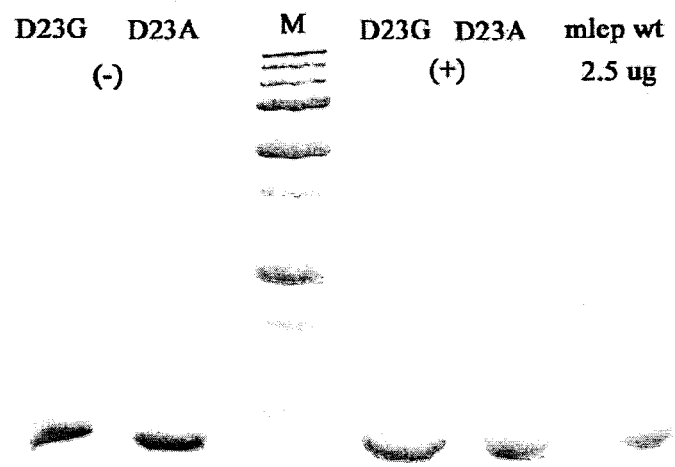
FIGS. 5A-C show SDS-PAGE of the 8 variants of mouse leptin antagonist (MLA) mutated at D23 and run on a 15% gel in presence (+) or absence (−) of β-mercaptoethanol. WT mouse leptin (mlep wt) was run as a control. The size of the molecular mass markers (from the top to bottom in kDa) were: 250, 150, 100, 75, 50, 37, 25, 20, 15 and 10.
Figure 5B:
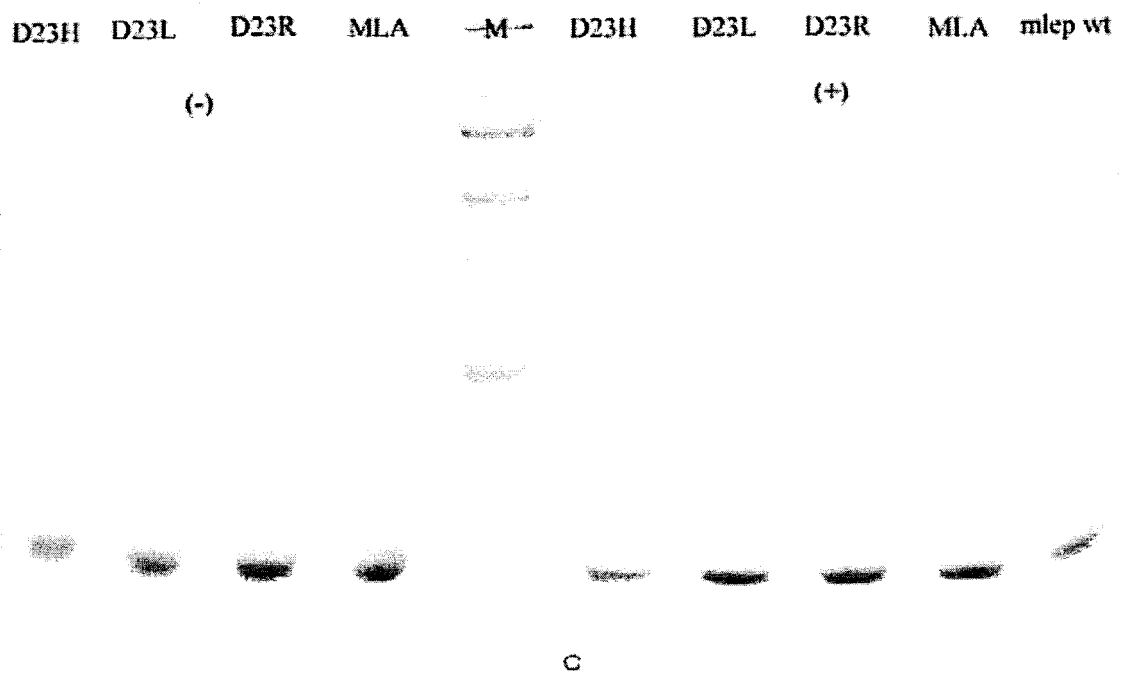
Figure 5C:
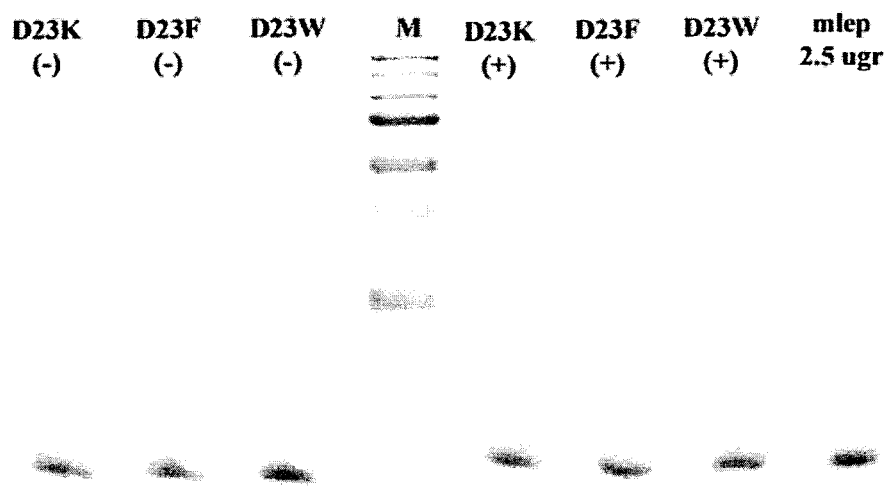
Figure 6A:
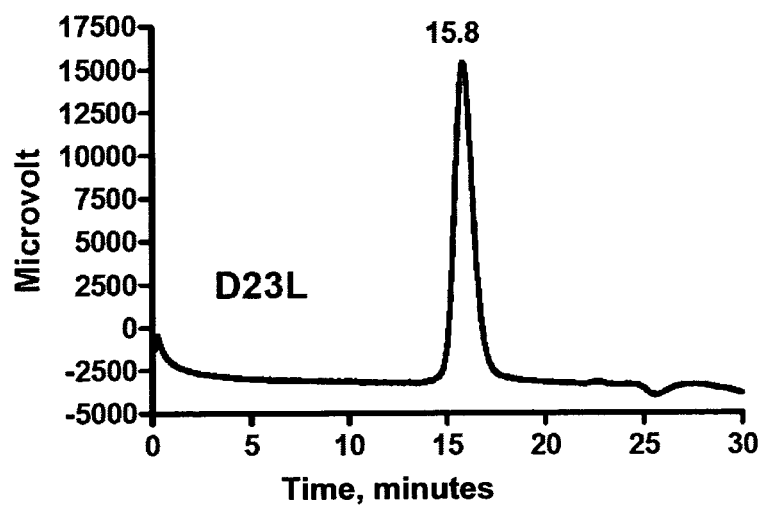
FIGS. 6A-H depict gel filtration analysis of 8 variants of MLA mutated at D23 developed on a Superdex 75 column at 0.8 ml/min in TN buffer, pH 8.
Figure 6B:
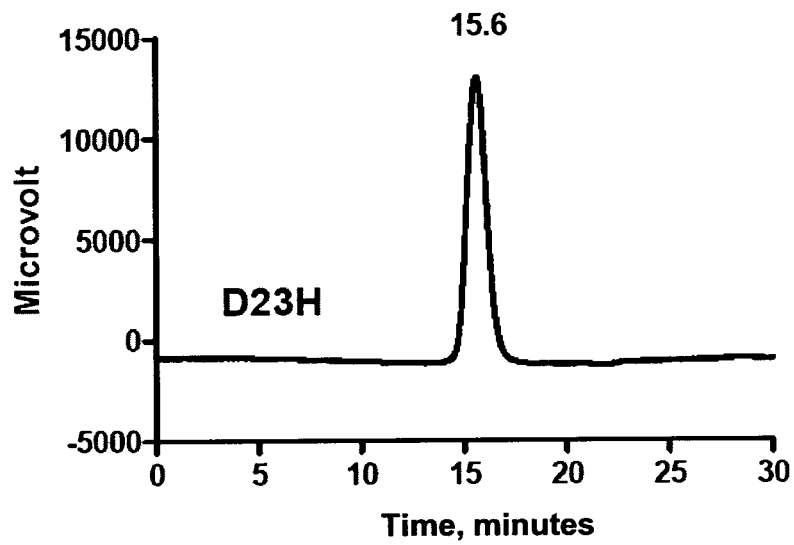
Figure 6C:
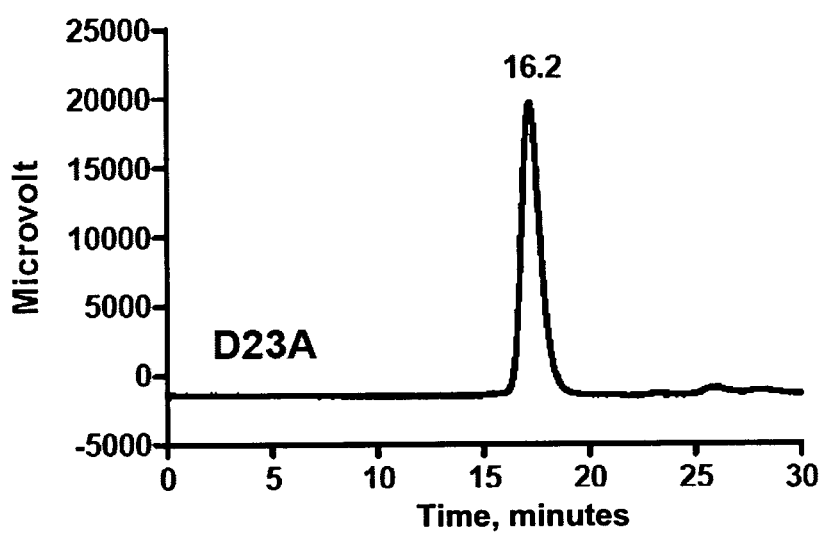
Figure 6D:
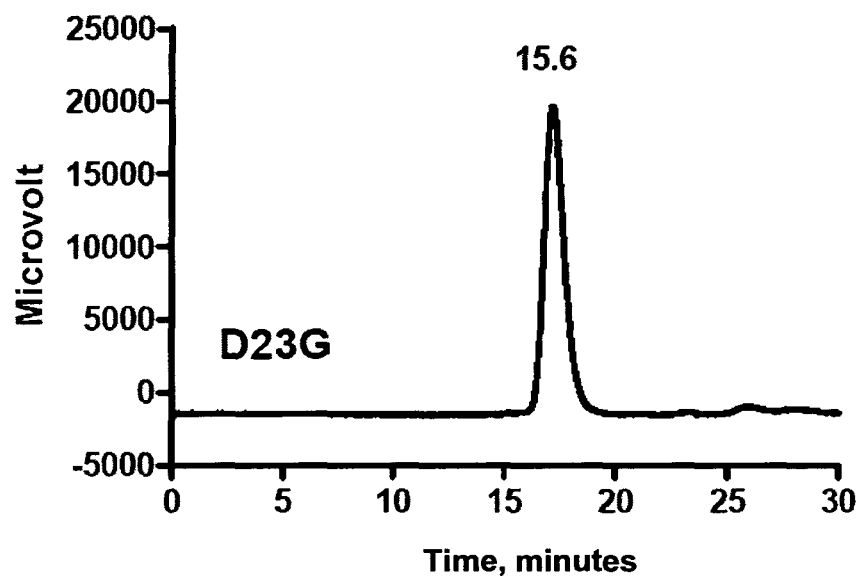
Figure 6E:
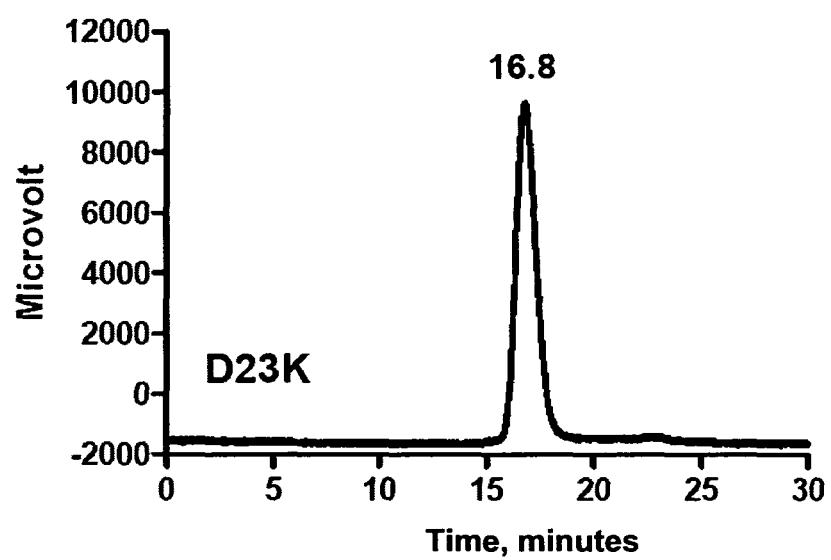
Figure 6F:
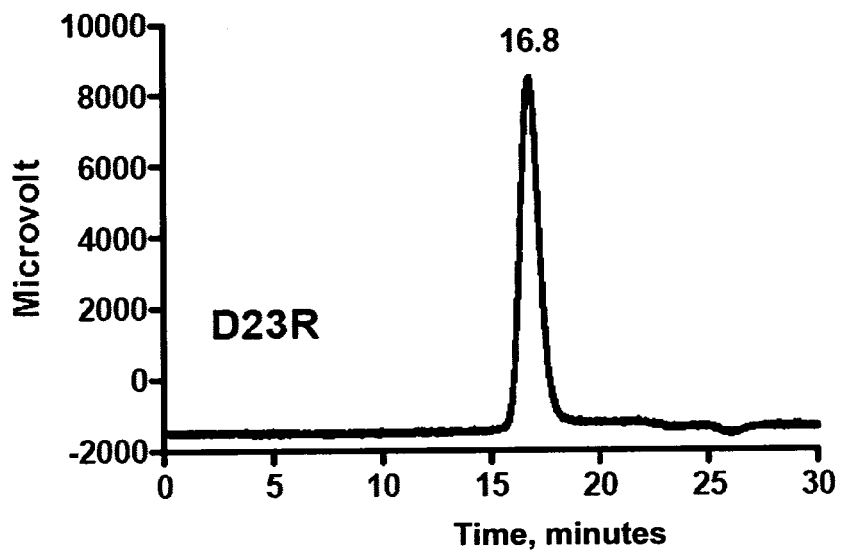
Figure 6G:
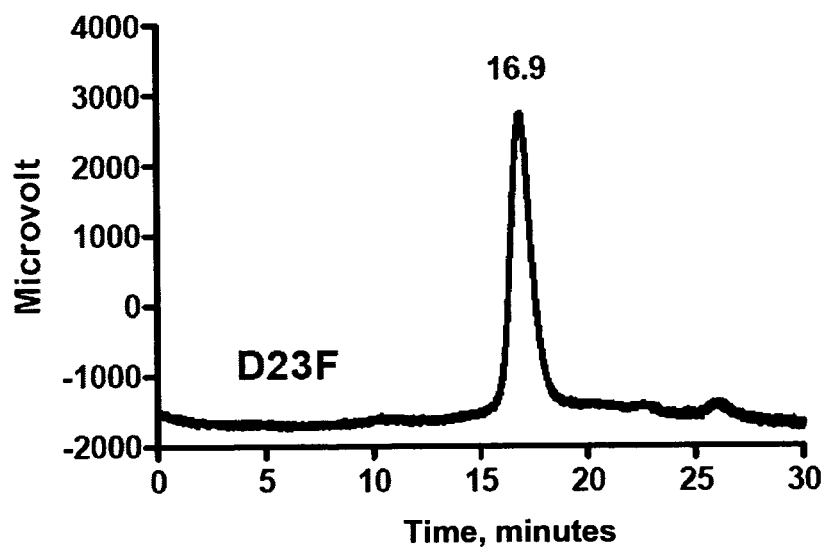
Figure 6H:
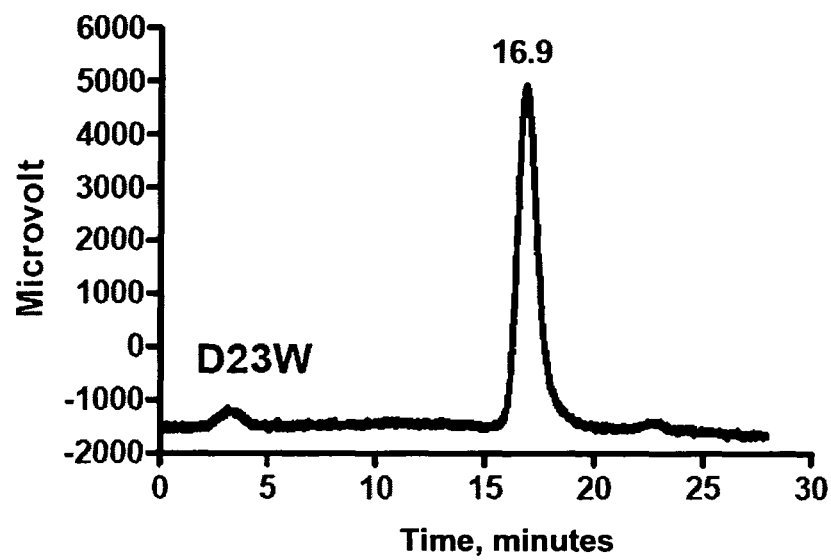
Figure 7A:
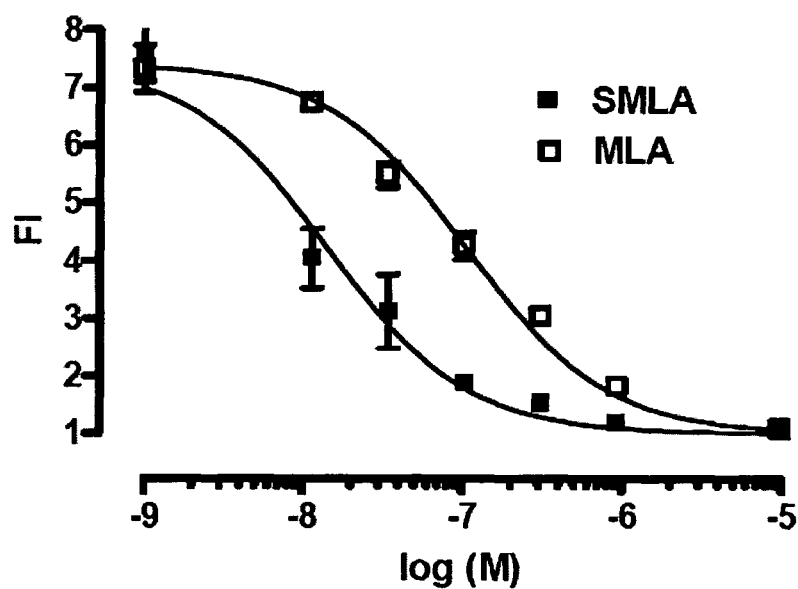
FIGS. 7A-D show comparison of biological activity (A, B) and binding properties (C, D) of mouse leptin antagonist (MLA) and super active MLA (SMLA) (A, C) and of polyethylene glycol (PEG)-MLA and PEG-SMLA (B, D). FI, fluorescence intensity.
Figure 7B:
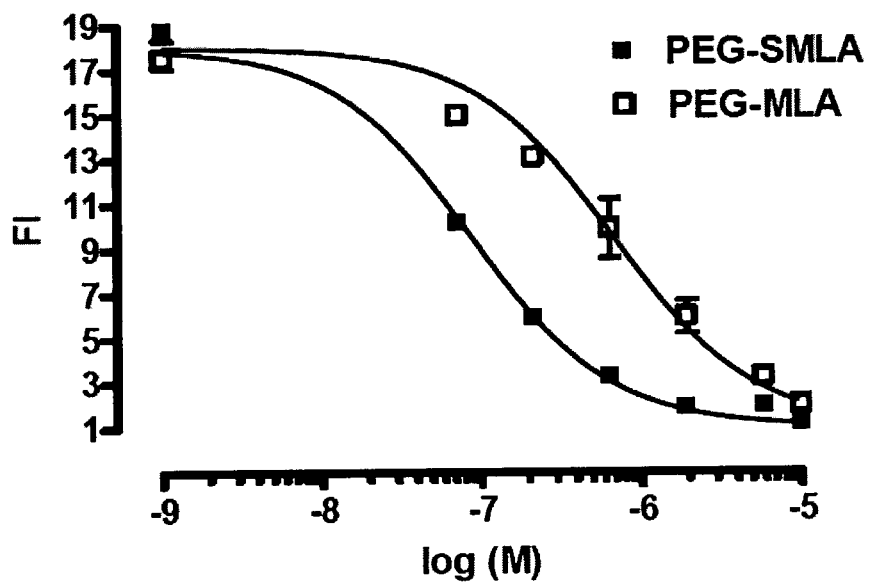
Figure 7C:
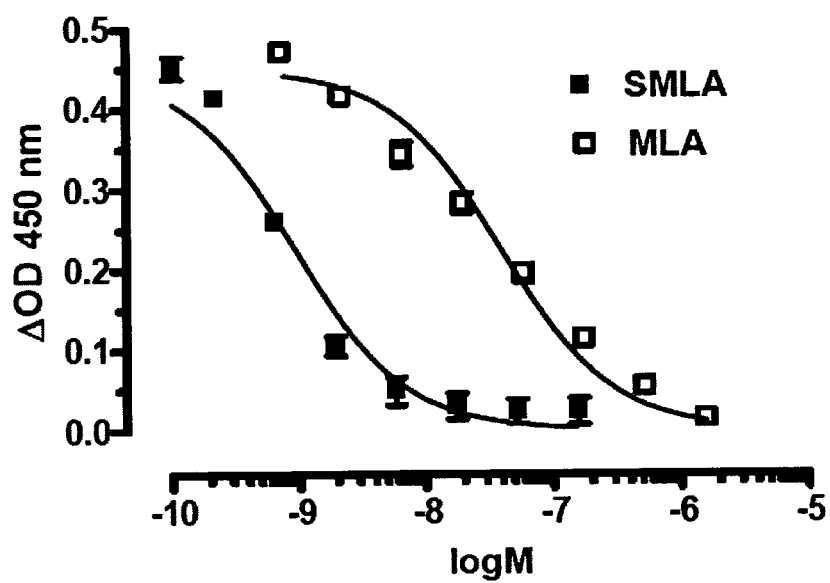
Figure 7D:
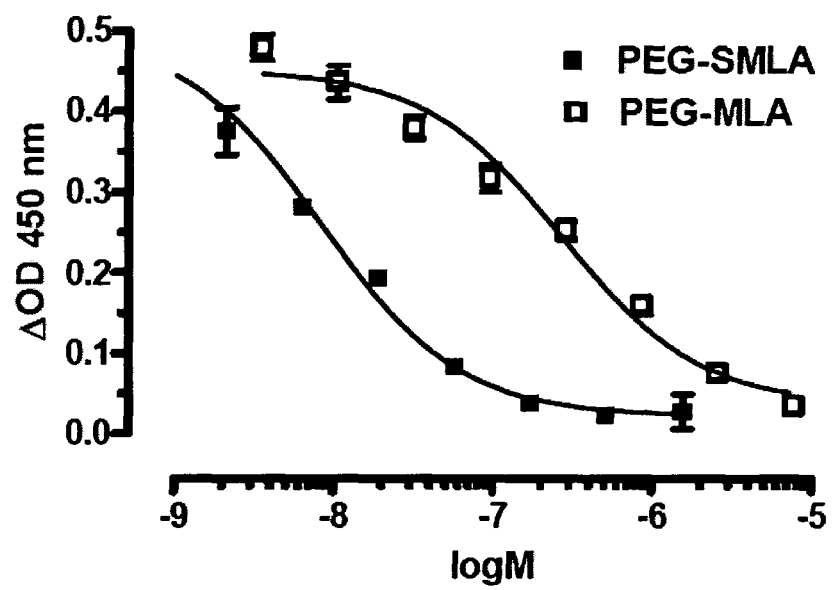
Figure 8A:
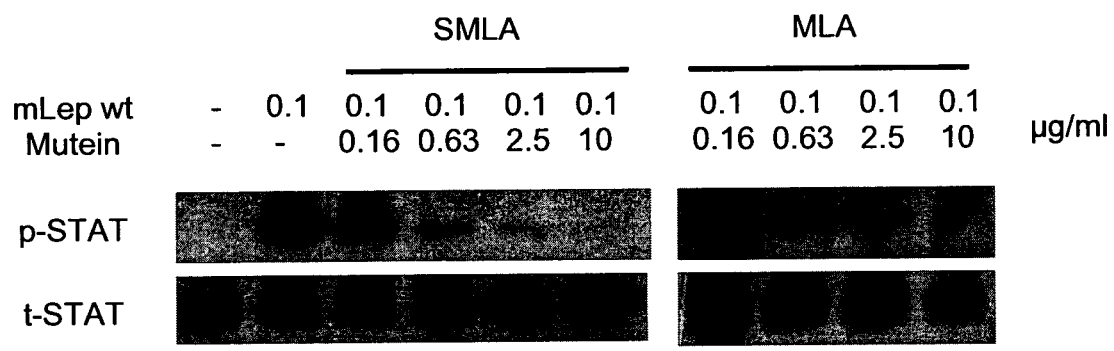
FIGS. 8A-B show a Western Blot (A) comparing inhibition of STATS phosphorylation by SMLA and MLA in CHO cells stably transfected with mouse OBRb. (B) quantification of the bands in (A) represented as a bar graph. FI, fluorescence intensity; D23L, SMLA. P-STAT, phosphorylated STAT; t-STAT, total STAT.
Figure 8B:
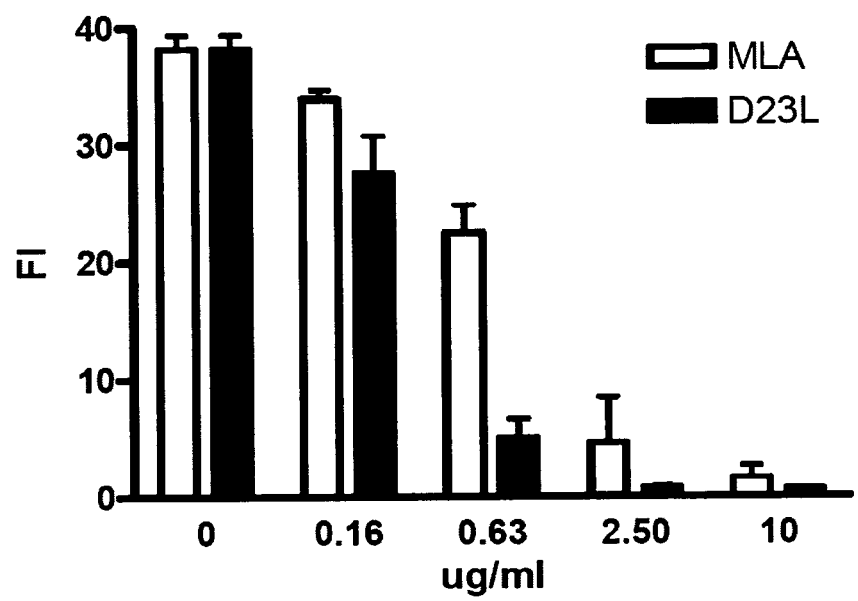
Figure 9A:
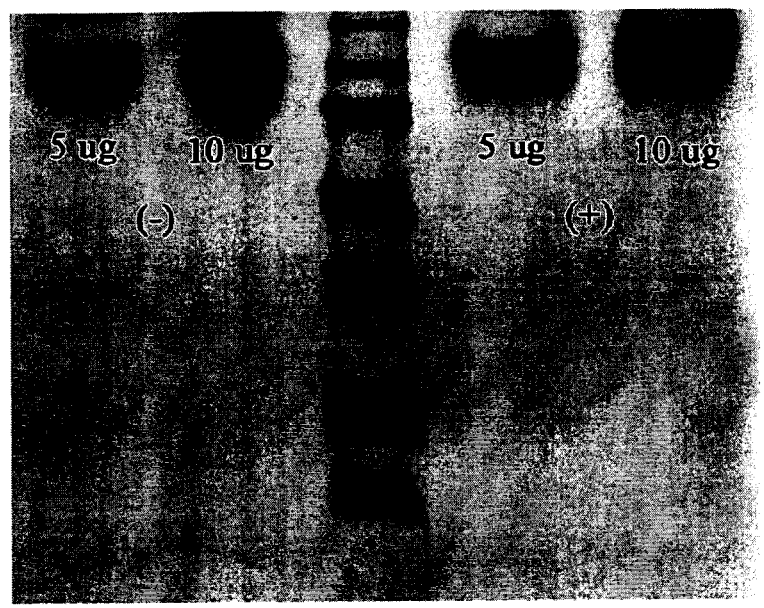
FIGS. 9A-B show (A) SDS-PAGE of PEG-SMLA run on a 12% gel in presence (+) or absence (−) of β-mercaptoethanol (The molecular mass markers (from the top to bottom in kDa) were: 150, 100, 75, 50, 37, 25 and 20) and (B) gel filtration analysis of PEG-SMLA on a Superdex 200 column at 0.7 ml/min in TN buffer, pH 8.
Figure 9B:
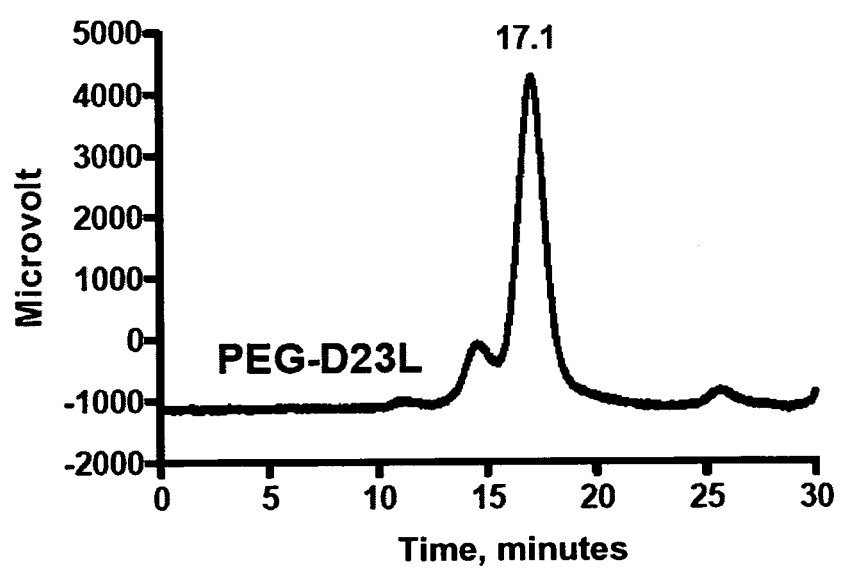

The approximate affinity of the surface displayed mouse leptin mutants was determined in situ on the cell wall by titrating whole cells with varying concentrations of biotinylated Equilibrium binding was measured by analyzing cell bound hLBD and c-myc positive in 13 distinct clones (identified in Table 2) by flow cytometry. Nonlinear regression (curve fit) of these data indicate about up to 2.3 fold increased affinity in 7 out of 13 leptin mutants (H30, H15, H22, H12, H16, H19 and H7) as shown in FIGS. 4A-B and Tables 3 and 4 (derived from FIGS. 4A and 4B, respectively). Those 7 mouse leptin mutants were selected for preparation of respectively mutated leptins expressed in *E. coli*.

TABLE 3

Affinity toward soluble human leptin receptor (hLBD) in 13 yeast clones selected after the third screening cycle (derived from FIG. 4A).

| Clone number* | Bmax | Kd |
|---|---|---|
| mlep, wt1 | 1063 | 158.7 |
| mlep, wt2 | 955.7 | 115.0 |
| H3 | 1446 | 91.68 |
| H7 | 1587 | 125.8 |
| H12 | 960.7 | 130.4 |
| H17 | 3599 | 619.6 |
| H19 | 968.2 | 104.2 |
| H22 | 852.3 | 122.3 |
| H30 | 846.7 | 59.46 |

*See Table 3

TABLE 4

Affinity toward soluble human leptin receptor (hLBD) in 13 yeast clones selected after the third screening cycle (derived from FIG. 4B).

| Clone number* | Bmax | Kd |
|---|---|---|
| mlep, wt1 | 848.7 | 94.978 |
| mlep, wt2 | 800.8 | 95.65 |
| H2 | 2566 | 243.2 |
| H3 | 1348 | 92.76 |
| H6 | 1288 | 99.06 |
| H7 | 1142 | 83.46 |
| H12 | 785.2 | 103 |
| H16 | 550.2 | 43.96 |
| H19 | 965.7 | 68.41 |
| H22 | 719.2 | 82.30 |
| H30 | 741.2 | 40.93 |
| L1 | 1678 | 157.7 |

*See Table 3

Example 2

Preparation and Characterization of Six Respective Mutants of Mouse Leptin and Mouse Leptin Antagonists Seven mutants of mouse leptin that were selected by yeast surface display screening (see above and in Table 5) were expressed in *E. coli*, refolded and purified as recombinant proteins by consecutive anion-exchange and gel-filtration chromatography as described in Materials and Methods section. As in initial experiments H7 mutant did not show any increase in the affinity, the corresponding L39A/L40A/F41A mutant was not prepared. To obtain respective 6 mouse leptin antagonists (MLAs), all six mutants were also inserted with the L39A/D40A/F41A mutations and purified respectively. All 13 proteins were tested for purity using SDS-PAGE and found >99% pure and their monomer content was more than 95% (not shown).

Determination of the Changes in Affinity and Biological Activity.

All 13 recombinant muteins (seven agonists and six antagonists) were tested for the eventual change in the binding properties by binding to immobilized hLBD and for their respective agonistic or antagonistic activity using the BAF/3 cells proliferation assay and by the activation of luciferase reporter gene in H-49 cells as described in Materials and Methods

TABLE 5

Mutations in the seven most active mouse leptin agonists screened by binding to hLBD

| Amino acid change | Clone H30 | Clone H19 | Clone H15 | Clone H16 | Clone H22 | Clone H12 | Clone H7 |
|---|---|---|---|---|---|---|---|
| K11R | | | | | | | X |
| T12I | | | | | X | | |
| D23G | | X | X | X | | | |
| D23H | X | | | | | | |
| Q34R | | | | | | | X |
| T37A | | X | | | | | X |
| G44D | | X | | | | | |
| L68M | | | X | | | | |
| F92C | | | | | | | X |
| S97F | | | X | | | | |
| S97Y | | | | | | X | |
| G112S | | | | X | | | |
| S132Y | | | X | | | | |
| I136V | | | | | | | X | section. As shown in Table 6, the most potent mutein was derived from clone H30 bearing the mutation D23H. However elevated activity was also found in proteins derived from clones H15, H16 and H19, all having the D23 mutated to Gly but also having additional mutations as shown in Table 3. In contrast, proteins derived from clone H12 showed no increase in affinity or in bioactivity. Only one protein derived from clone H22, lacking the D23 mutation but having only one mutation (T12I) showed a moderated increase in affinity and bioactivity (the latter found in antagonist only).

To check whether the T12I mutation may have an additive effect to that of D23 we prepared 3 double mutants (T12I/D23H, T12I/D23R and T12I/D23L) of MLA but neither their inhibitory activity in BAF/3 bioassay nor their binding affinity toward hLBD were superior to that of D23H or D23R or D23L MLA respectively (not shown). Interestingly, whereas the changes in the binding properties of the agonists and antagonists were highly comparable, the biological activity was elevated only in the antagonists.

Example 3

Rational Mutagenesis of D23 in MLA to Seven Variants

In view of the former results (see above) showing that D23H mutation alone was sufficient for maximal increase of biological activity of MLA, total of seven mutated plasmids in which D23 was replaced by small (G, A) or hydrophobic (L, F, W) or positive

TABLE 6

Binding properties and biological activity in the six mutants of mouse leptin and 7 mutants of mouse leptin antagonist prepared in E. coli.

| Mutant | Binding assay* | BAF/3 bioassay* | Luciferase bioassay* |
|---|---|---|---|
| Mouse leptin | | | |
| H30 | 35.0 ± 2.00 (2) | 0.3 ± 0.06 (3) | 0.6 (1) |
| H15 | 9.7 ± 1.01 (2) | 0.5 ± 0.08 (3) | 0.8 (1) |
| H22 | 11.7 ± 0.20 (2) | 0.8 ± 0.21 (3) | 0.7 (1) |
| H12 | 1.5 ± 0.00 (2) | 0.9 ± 0.16 (3) | 0.7 (1) |
| H16 | 20.3 ± 1.25 (2) | 0.8 ± 0.04 (3) | 0.9 (1) |
| H19 | 10.4 ± 2.90 (2) | 0.9 ± 0.19 (3) | 1.5 (1) |
| H7 | 0.83 ± 0.17 (2) | 0.5 ± 0.12 (2) | 0.3 (1) |
| Mouse leptin antagonists | | | |
| H30 (antagonist) | 34 ± 3.15 (8) | 5.0 ± 0.34 (5) | 5.7 ± 1.42 (4) |
| H15 (antagonist) | 12.4 ± 0.60 (2) | 4.8 ± 1.09 (3) | 4.2 ± 0.69 (3) |
| H22 (antagonist) | 11.2 ± 0.80 (2) | 2.4 ± 0.51 (2) | 3.3 ± 0.20 (3) |
| H12 (antagonist) | 1.4 ± 0.48 (2) | 0.8 ± 0.21 (3) | 0.1 ± 0.04 (3) |
| H16 (antagonist) | 11.0 ± 3.90 (2) | 3.3 ± 0.21 (3) | 3.3 ± 0.64 (3) |
| H19 (antagonist) | 6.1 ± 1.05 (2) | 3.5 ± 0.26 (2) | 2.9 ± 1.35 (3) |

*the numbers show the fold increase in affinity or bioactivity as compared to the WT mouse leptin or WT mouse leptin antagonist and are given as mean ± SEM. The numbers of performed experiments are given in parentheses.

charged (K, R) amino acids were prepared by rational mutagenesis as described in Materials and Methods. All seven mutants were purified as recombinant proteins by consecutive refolding, dialysis, anion-exchange and gel-filtration chromatography and found pure by SDS-PAGE and containing more than 98% of monomer (FIGS. 5A-C, 6A and 6H). All those mutants were tested for the binding affinity toward hLBD and for their biological inhibitory potency in the BAF/3 proliferation assay. The results summarized in Table 7 show that the D23L mutation resulted in the highest activity. It was therefore decided that this mutant will be prepared in large scale experiments, pegylated and used for in vivo experiments.

TABLE 7

Activity summary of mouse leptin antagonists D23 mutants

| Mutant | Binding assay* | BAF/3 bioassay* | Luciferase bioassay* |
|---|---|---|---|
| D23H | 34 ± 3.15 (8) | 5.0 ± 0.34 (5) | NT |
| D23G | 17.5 ± 4.50 (2) | 2.5 ± 0.05 (2) | NT |
| D23A | 21 ± 1.00 (2) | 3.3 ± 0.75 (2) | NT |
| D23L | 64 ± 5.82 (6) | 13.9 ± 0.55 (2) | 13.4 ± 1.50 (7) |
| D23K | 19 ± 9.00 (2) | 3.7 ± 0.35 (2) | NT |
| D23R | 51 ± 3.95 (6) | 8.6 ± 1.15 (2) | NT |
| D23F | 28 ± 3.56 (4) | 3.7 ± 0.25 (2) | NT |
| D23W | 36 ± 6.02 (4) | 4.2 ± 1.7 (2) | NT |

*the numbers show the fold increase in affinity or bioactivity as compared to the WT mouse leptin antagonist. The numbers of performed experiments are given in parentheses. NT—not tested.

Large-Scale Purification and Pegylation of Mouse Leptin D23L/L39A/D40L/F41A Antagonist.

Prolonging of the refolding in 4.5 M urea from 2 to 48 h prior to dialysis (see Materials and Methods) dramatically improved the yield of the monomeric fraction of the D23L/L39A/D40L/F41A mouse leptin antagonist and the final yield of the protein purified from the IBs corresponding to 3 L of fermentation mixture varied between 400 to 500 mg. The protein designed as a superactive MLA (SMLA) was >99% pure by SDS-PAGE and contained more than 95% monomer (see the respective mutant in FIGS. 5A-C and 6A). Its binding affinity toward hLBD was increased 64-folds and its biological activity in vitro in BAF/3 or H-49 cell bioassays was increased by 13.9 and by 13.4 fold (see Table 7 and FIGS. 7A and 7C). The comparative biological activity of MLA and SMLA was also tested in a semi-quantitative STATS phosphorylation bioassay, showing at least 5-fold higher activity of the latter (FIGS. 8A-B). Pegylation of this protein carried out by the method previously described for pegylation of MLA resulted in lower yield varying between 55 to 75 mg of pegylated protein from 400 mg of non pegylated SMLA.

The final preparation of PEG-SMLA was pure by SDS-PAGE criteria and contained ~9% of double pegylated SMLA, 85% of monopegylated SMLA and less than 1% of non-pegylated SMLA (FIGS. 9A-B). Although as shown by a representative experiment in FIGS. 7B and 7D, the biological activity in H-49 cells and the affinity toward hLBD of the pegylated SMLA were reduced respectively by 9- and 6.2fold as compared to the non-pegylated SMLA. Those changes were comparable to the pegylation effect of MLA as shown in FIGS. 7A and 7C (7 and 6.3 respectively) and in our recent publication (Elinav et al. 2009b).

Example 4

Weight Gain Experiments in Mice

For assessment of the in-vivo activity of SMLA, 6.25 mg/kg vehicle, pegylated-MLA, or pegylated SMLA were intraperitoneally administered to 7-week-old female C57bl mice. As depicted in FIG. 10 and as published before (Elinav et al., 2009), control mice maintained stable weight (99%±0.5) while PEG-MLA induced a significant weight gain that was statistically significant by day 5 and reached a level of 121%±1.4, stabilizing after 8 days of treatment. In comparison, PEG-SMLA induced a weight gain that peaked to 143.4%±3.15 (mean±SEM) on day 17, and stabilized thereafter. The differences in weight gain between PEG-MLA and PEG-SMLA were statistically-significant from day 6 and thereafter. Weight gain was mediated by differences in food consumption that was significantly higher in pegylated-SMLA treated mice (4.02±0.17 g/d/mouse) as compared to both pegylated-MLA (3.17±0.56 g/d/mouse) and control mice (2.54±0.14 g/d/mouse, $P<0.01$). Throughout the experiment, mice looked healthy and active with no gross evidence of stress. On day 20, 3 mice of each of the groups were sacrificed. The remaining mice in each group were taken off the treatments and watched for resolution of the weight gain. Within the next 17 days, (FIG. 10) mouse weights were drastically reduced. In an additional experiment aimed at dose-related comparison of PEG-MLA and PEG-SMLA several daily doses of both proteins (20, 6.7, 2.2 and 0.73 mg/kg) were compared. The results are provided in FIG. 11. In all 4 concentrations the weight gain induced by PEG-SMLA was significantly higher than the respective effect of PEG-MLA. The maximal almost identical effect (45% gains) was obtained by PEG-SMLA at 20 and 6.7 mg/kg. At 2.2 mg/day of PEG-SMLA the effect was lower but still superior to 20 mg/kg of PEG-MLA, indicating at least 10-fold higher potency of the former. Interestingly, in up to 11 days both treatments gave comparable results but thereafter the effect of PEG-MLA leveled off, while mice treated with PEG-SMLA continued to gain weight until at day 16 the difference became significant ($P<0.05$). On days 7-11, the lowest dose of PEG-SMLA (0.72 mg/kg) induced significantly lesser weight gain than 20 mg/kg PEG-MLA, but reached the same value on days 15 and 16. This indicates that PEG-SMLA's actual efficacy is up to 27-fold greater than that of PEG-MLA.

TABLE 8

Average food and water intake in mice daily injected with PEG-MLA or PEG-SMLA. Both materials were injected daily at 20, 6.7, 2.2 and 0.72 mg/kg for a period of 17 days. The results are mean ± SEM, n = 8.

| Treatment | Dose (mg/kg) | Food intake (g/day) | Water intake (ml/day) |
|---|---|---|---|
| PEG-SMLA | 20 | 4.82 ± 0.29$^a$ | 5.69 ± 0.49$^a$ |
| " | 6.7 | 4.54 ± 0.26$^a$ | 4.51 ± 0.35$^{ab}$ |
| " | 2.2 | 4.01 ± 0.23$^{ab}$ | 4.36 ± 0.32$^{ab}$ |
| " | 0.72 | 3.34 ± 0.16$^{bc}$ | 4.15 ± 0.23$^{bc}$ |
| PEG-MLA | 20 | 3.58 ± 0.24$^b$ | 4.52 ± 0.25$^{ab}$ |
| " | 6.7 | 3.36 ± 0.18$^{bc}$ | 4.82 ± 0.29$^{ab}$ |
| " | 2.2 | 3.12 ± 0.15$^{bc}$ | 5.32 ± 0.60$^{ab}$ |
| " | 0.72 | 3.05 ± 0.13$^{bcd}$ | 4.38 ± 0.24$^{ab}$ |
| Control | none | 2.87 ± 0.13$^{cd}$ | 4.02 ± 0.29$^b$ |

$^{a,b,c,d}$All groups not designated with same letter are significantly different (p < 0.05).

There was strong correlation between the weight gain and the food intake, as shown in Table 8. In contrast there was almost no difference in water intake, confirming leptin antagonist's specific effects on appetite rather than on thirst regulatory pathways.

Example 5

Figure 12A:
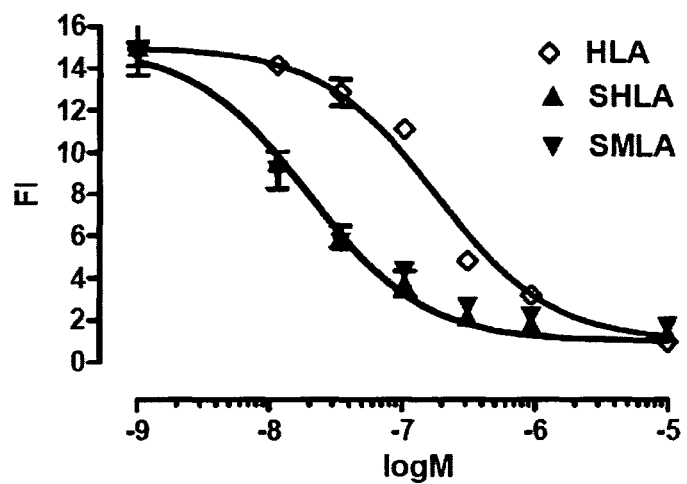
FIGS. 12A-D show comparison of biological activity (A, B) and binding properties (C, D) of HLA, SHLA, SMLA, PEG-HLA and PEG-SHLA. FI, fluorescence intensity.
Figure 12B:
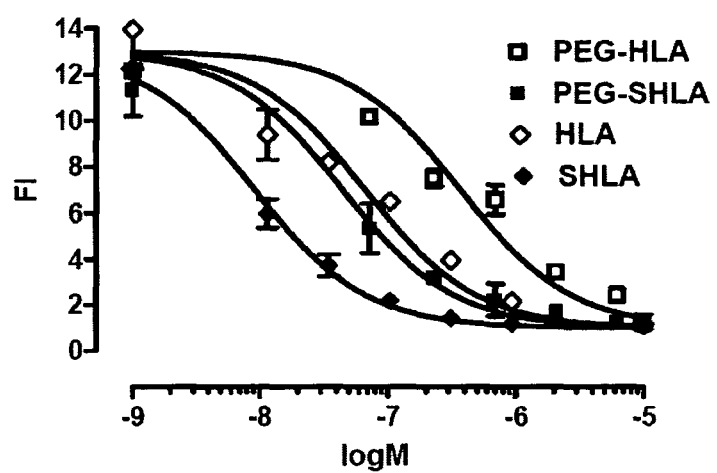
Figure 12C:
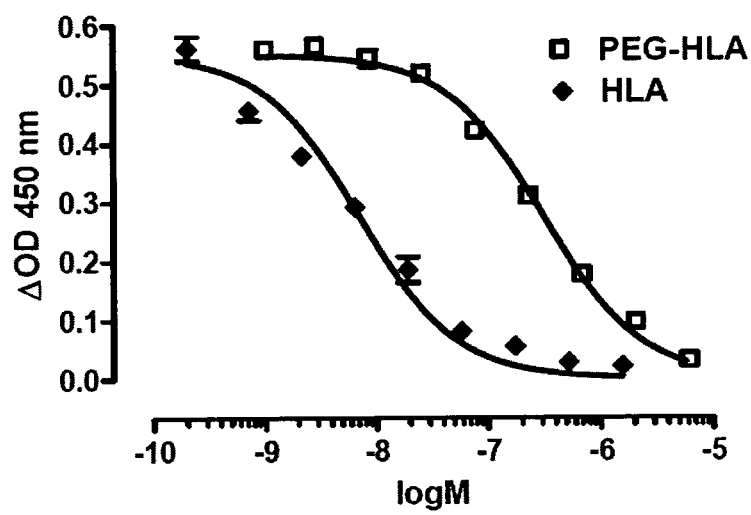
Figure 12D:
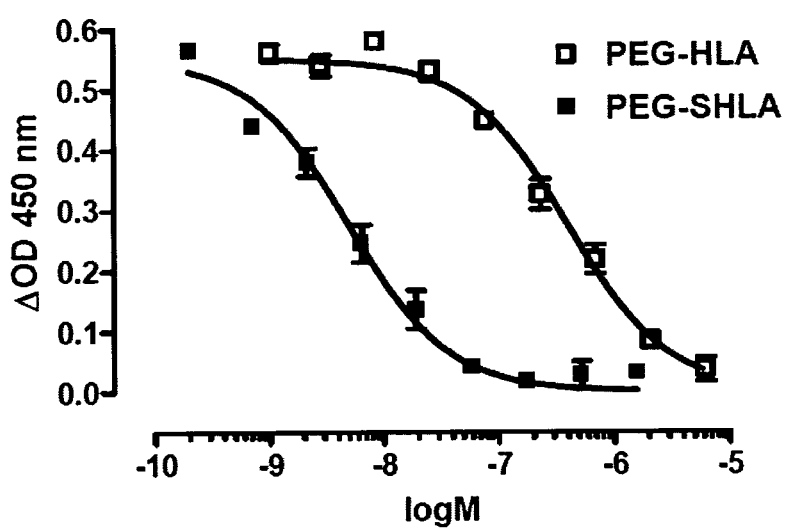

Preparation and Characterization of Human and Ovine Leptin Antagonist (HLA) with Increased Affinity Toward Leptin Receptor In order to verify that D23L mutation increases the affinity of leptin antagonist to leptin receptor and subsequent biological activity not only in MLA but also in analogous leptin antagonists corresponding mutants (D23L/L39A/D40A/F41A) were prepared by rational mutagenesis, expressed in large scale in *E. coli*, purified to homogeneity and termed SHLA (human) or SOLA (ovine). The purified protein was pure as determined by SDS-PAGE under reducing and non-reducing condition and appeared as >98% monomer in gel filtration experiments (not shown). To facilitate the use of SHLA and SOLA for in vivo experiments they were pegylated similarly to SMLA (see above) and termed PEG-SHLA and PEG-SOLA, respectively. SHLA, PEG-SHLA, SOLA and PEG-SOLA were tested for binding and inhibitory activity according to the methods previously described for MLA, SMLA and their pegylated derivatives (see FIG. 12 for human proteins; results for ovine proteins not shown). As shown (FIG. 12A) SMLA and SHLA exhibited identical biological activity which was >9-folds higher than that of HLA. This result was verified in an additional experiment and a similar relative increase in the activity was also observed in PEG-SHLA vs PEG-HLA (FIG. 12B). FIG. 12C and FIG. 12D show that the increase of biological activity due to D23L mutation origins from the dramatic (44-fold and 80-fold) increase in the affinity for the immobilized hLBD.

In a preliminary in vivo weight-gain experiment in mice (12.5 mg/kg/day, lasting for 2 weeks), PEG-MLA and PEG-HLA were compared both showing identical effect weight-gain effect (not shown). Therefore to validate the effect of D23L mutation, similar comparative in vivo experiment was carried out with PEG-SHLA and PEG-SMLA. The results are presented in FIGS. 13A-B and show that both materials exhibited similar weight gain effect.

Example 6

Figure 15A:
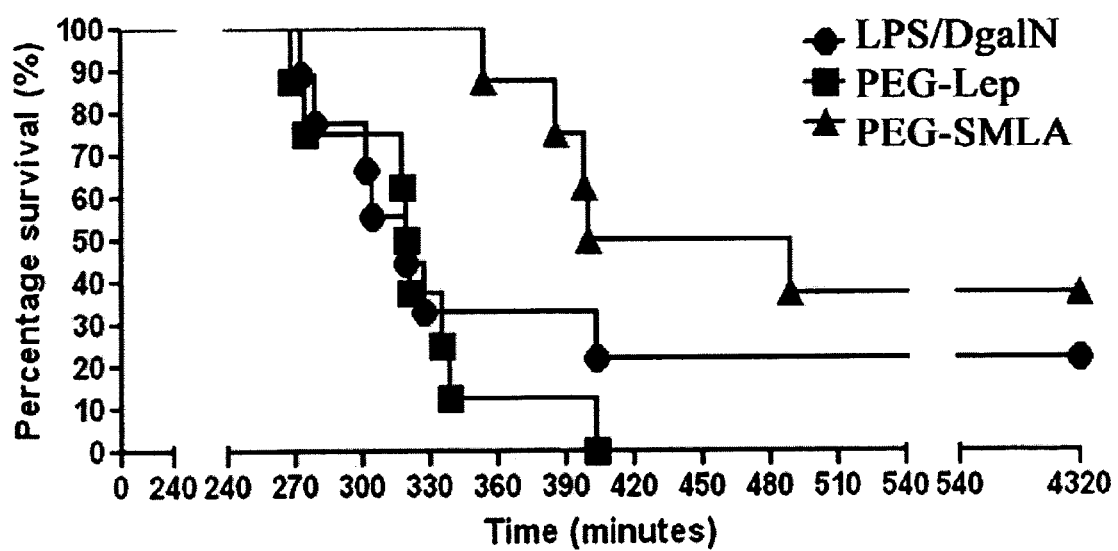
FIGS. 15A-B show that superactive leptin antagonist induces protection from innate inflammation by inhibition of infiltrating mononuclear phagocytes. PEG-SMLA (20 mg/kg) or PEG-leptin (PEG-Lep; 0.4 mg/kg) were administered intraperitoneally to female C57bl mice for 4 days. This was followed by induction of hepatitis induced by activation of the innate immune response via administration of Lypopolysachamide (LPS; 10 ug/kg) and D-Galactoseamine (DgalN; 600 mg/kg) at time zero. Steady state, cell population at the time period before administration of LPS and DgalN; 1.5 hrs LPA/D-GalN, cell population at the time period 1.5 hrs after administration of LPS and DgalN; The populations of hepatic CD45+CD11b+CD11−F4/80+infiltrating and resident macrophage population are depicted in gate P4 and gate P5, respectively; CD11b and F4/80 are markers for macrophages.

Superactive Leptin Antagonist Induces Protection from Innate Inflammation by Inhibition of Infiltrating Mononuclear Phagocytes PEG-SMLA (20 mg/kg) or PEG-leptin (0.4 mg/kg) were administered intraperitoneally to female C57bl mice for 4 days. This was followed by induction of innate hepatitis via administration of Lypopolysachamide (10 ug/kg) and D-Galactoseamine (600 mg/kg), a known model for the induction of hepatitis induced by activation of the innate immune response through infiltrating and TNF-a secretion by mononuclear phagocytes. As is depicted in FIG. 15A, administration of PEG-leptin resulted in significantly enhanced mortality as compared to vehicle treated mice. In contrast, administration of PEG-SMLA resulted in significant protection, manifesting as improved survival of mice.

Figure 15B:
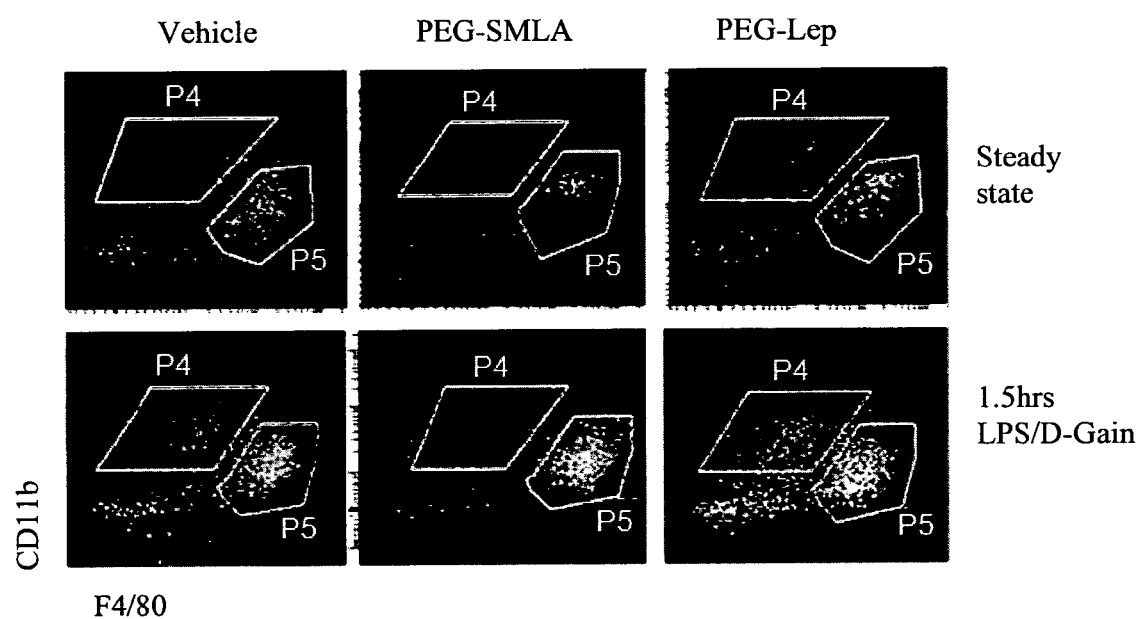

To test the effect of leptin antagonism on the effector infiltrating macrophages (FIG. 15B), The population of hepatic CD45+CD11b+CD11−F4/80+infiltrating (FIG. 15B, gate P4) and resident (FIG. 15B, gate P5) macrophage population were tested in vehicle, leptin antagonist and leptin-agonist-treated mice. As seen in FIG. 15B, lower panels, the leptin antagonist-mediated protective effect was accompanied by a dramatic reduction in the inflammation-induced population of liver-infiltrating macrophages as compared to vehicle-treated mice. A reverse phenotype was noted in mice treated with PEG-leptin, in which liver macrophage infiltration was enhanced in leptin-agonist-treated mice as compared to vehicle-treated mice.

Importantly, even at steady state before induction of innate inflammation (FIG. 15B, upper panels), the reduction in infiltrating macrophages in superactive leptin antagonist-treated mice was substantially lower as compared to untreated mice. The reverse phenotype was seen also in steady state in leptin agonist-treated mice, which featured an expanded macrophage infiltration, already during steady state.

Altogether, these results demonstrate a significant protective effects of the superactive leptin antagonist in innate immune-mediated inflammation, mediated by inhibition of mononuclear macrophage infiltration into the inflamed organ.

Example 7

Insulin-Resistance and Diabetes Type II Model in Mice

Figure 13A:
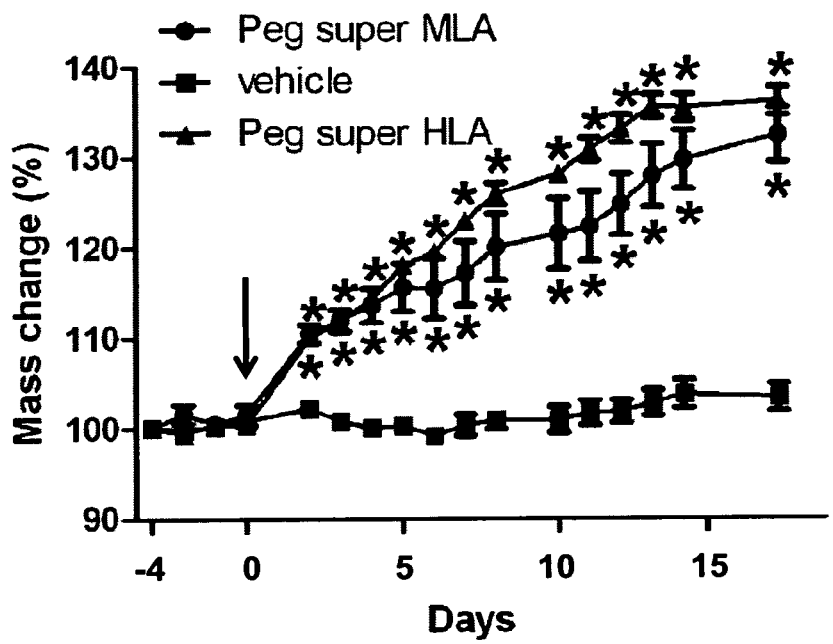
FIGS. 13A-B shows comparison of the effect of PEG-SMLA and PEG-SHLA on weight gain in female mice (A). Both materials were injected daily at 6.25 mg/kg for 17 days starting at time zero (arrow). In (B) we see average comparative food and water intake. At all points marked with * both treatments were significantly ($p<0.05$) different from the vehicle but not between themselves. The results are mean±SEM, n=8. PEG-SMLA, PEG-super mouse leptin antagonist; PEG-SHLA, PEG-super human leptin antagonist.
Figure 13B:
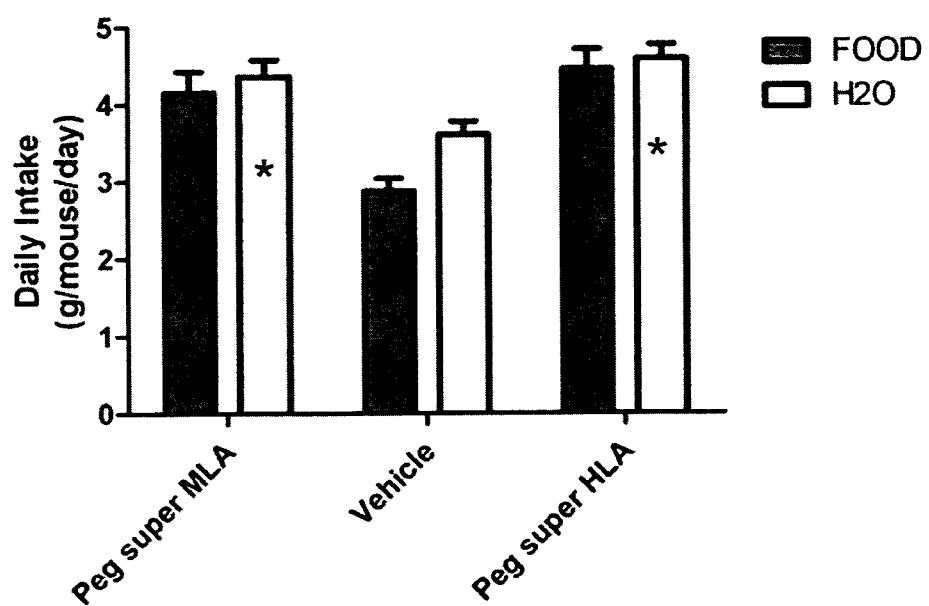

Pegylated leptin antagonists (PEG-MLA) and even more (PEG-SMLA) induced very strong orexigenic effect in both male and female mice, leading to a very fast (up to 40-50%) weight gain originating mainly from fat accumulation (FIG. 13A). This weight gain could be reversed upon ceasing PEG-MLA or PEG-SMLA injections. In an additional experiment male mice (n=16) injected with PEG-MLA (20 mg/kg/day) for 21 days gradually developed insulin resistance and the difference in insulin level and homeostatic model assessment (HOMA) score compared to the controls was significant (p<0.05). HOMA is a method used to quantify insulin resistance and beta-cell function. In longer term experiments (up to 60 days), a significant increase in blood glucose, blood triglycerides and total cholesterol was also observed—an indication of the appearance of prediabetic metabolic syndrome. However, up to 2 months treatment did not lead to liver damage as evidenced by the level of liver enzymes in blood.

In a short term metabolic experiment, male mice, acclimatized to a metabolic chamber, received morning, sub cutaneous injections of either PEG-SMLA (5 mg/kg/day) or vehicle. These injections were repeated 24 h later and the mice studied in a metabolic chamber for 48 h, beginning with the first injection and ending 24 h after the second injection. By the end of the 2nd 24 h period, mice that had received SMLA weighed 3 g more than those receiving vehicle (p<0.05), had an increase in RQ consistent with conservation of fat mass (p<0.05), and a reduction in activity (p<0.05).

In conclusion this reversible leptin antagonists-induced obesity, associated with hyperglycemia, hyperlipidemia and insulin resistance may serve as a fast reversible model of diabetes mellitus type 2 in mice. Such a model can be achieved by injection of PEG-SMLA or by creation of transgenic mice expressing conditionally the DNA sequence encoding the SMLA.

Methods for producing transgenic mice are common knowledge and any appropriate method may be chosen for producing the transgenic mice of the present invention, for example according to the following steps:

DNA Preparation for Microinjection or Electroporation

1) The DNA digest is separated on an agarose gel: Once the run is completed, the gel is stained with a fairly low concentration of EtBr. When finished staining, the gel is visualized using longwave UV, and cut the band of interest.

2) The DNA fragment is purified using for example a GeneClean spin column (BIO 101'S GeneClean Spinkit 3) The DNA is precipitated and resuspended in appropriate solvent.

Pronuclear Injections:

1) Egg Production for injections: To obtain a large quantitiy (>250) of eggs for injection, sexually immature FVB/N females are superovulated by using consecutive Pregnant mare's serum (PMS) and human chorionic gonadotropin (HCG) hormone injections. Females are mated to stud males immediately following the HCG injection.

2) Harvesting the eggs: Eggs are harvested the next day from the ampulla of the oviduct of the mated females. Eggs are treated with hyaluronidase to remove nurse cells, and are then washed.

3) Injecting the eggs: 30-50 eggs are removed from the incubator at a time for injection. Each egg is individually injected with the DNA fragment of the day under high magnification. When each egg in that group has been injected, all the eggs are returned to the incubator. This procedure is repeated until all eggs have been injected. At the end of the injection period, eggs which have not survived injection are removed from each group.

4) Implanting the eggs: Injected eggs are then implanted in groups of 10-15 bilaterally into the oviduct of pseudopregnant females (females which have been mated to vasectomized males). The animals are allowed to recover from anaesthesia on a warming plate, and then returned to the animal room. They are kept under sterile conditions throughout their pregnancy.

Tail DNA Preps for Genomic Southern Blot Analysis:

1) Digestion of the tail clip: Cut about 50-100 mgs of tail into an eppendorf tube and digest with protease.

2) Isolate the DNA with phenol/chloroform and rinse in ethanol.

3) Cut the DNA with appropriate restriction enzymes and perform a Southern Blot.

Mating Protocol

1) Determine the age of your mice: Minimum breeding age: males: 35-42 days; females: 21 days. Maximum age for first breeding: males and females: 6 months.

2) To breed, put the female into the male's cage. Reversing this order can result in the male killing the female (or, on rare occasions, the female killing the male). If it is not possible to put the female into the male's cage, use a clean cage, and put the male in the cage first. If this can be done one week in advance of the anticipated mating, this will allow the male to mark his territory, and the pheromone level to rise, which will aid in the breeding process.

The above protocol is an example. Other examples, and more details, are found in for example "Transgenic animal technology: a laboratory handbook, 2nd edition (Carl A. Pinkert, ed., Gulf Professional Publishing, 2002), which is hereby incorporated in its entirety.

REFERENCES

Bluher S, Shah S, Mantzoros C S (2009) Leptin deficiency: clinical implications and opportunities for therapeutic interventions. J Investig Med 57:784-8

Boder E T, Wittrup K D (1997) Yeast surface display for screening combinatorial polypeptide libraries. Nat Biotechnol 15:553-7

Boder E T, Wittrup K D (2000) Yeast surface display for directed evolution of protein expression, affinity, and stability. Methods Enzymol 328:430-44

Chao G, Lau W L, Hackel B J, Sazinsky S L, Lippow S M, Wittrup K D (2006) Isolating and engineering human antibodies using yeast surface display. Nat Protoc 1:755-68

Choi J H, Choi K C, Auersperg N, Leung P C (2004) Overexpression of follicle-stimulating hormone receptor activates oncogenic pathways in preneoplastic ovarian surface epithelial cells. J Clin Endocrinol Metab 89:5508-16

Chong A Y, Lupsa B C, Cochran E K, Gorden P. (2010) Efficacy of leptin therapy in the different forms of human lipodystrophy Diabetologia. 53:27-35

Elinav E, Ali M, Bruck R, Brazowski E, Phillips A, Shapira Y, Katz M, Solomon G, Halpern Z, Gertler A (2009a) Competitive inhibition of leptin signaling results in amelioration of liver fibrosis through modulation of stellate cell function. Hepatology 49:278-86

Elinav E, Gertler A (2009) Use of leptin antagonists as anti-inflammatory and anti-fibrotic reagents. In: Gertler A (ed) Leptin and leptin antagonists. Landes Bioscience, pp 133-140

Elinav E, Niv-Spector L, Katz M, Price T O, Ali M, Yacobovitz M, Solomon G, Reicher S, Lynch J L, Halpern Z, Banks W A, Gertler A (2009) Pegylated leptin antagonist is a potent orexigenic agent: preparation and mechanism of activity. Endocrinology 150:3083-91

Frankenberry K A, Skinner H, Somasundar P, McFadden D W, Vona-Davis L C (2006) Leptin receptor expression and cell signaling in breast cancer. Int J Oncol 28:985-93

Gertler A, Niv-Spector L, Reicher S (2007) Is leptin an important physiological regulator of CRP? Nat Med 13:18-9; author reply 19-21

Gertler A, Simmons J, Keisler D H (1998) Large-scale preparation of biologically active recombinant ovine obese protein (leptin). FEBS Lett 422:137-40

Iserentant H, Peelman F, Defeau D, Vandekerckhove J, Zabeau L, Tavernier J (2005) Mapping of the interface between leptin and the leptin receptor CRH2 domain. J Cell Sci 118:2519-27

La Cava A, Matarese G (2004) The weight of leptin in immunity. Nat Rev Immunol 4:371-9

Laemmli U K (1970) Cleavage of structural proteins during the assembly of the head of bacteriophage T4. Nature 227:680-5

Lowman H B, Wells J A (1993) Affinity maturation of human growth hormone by monovalent phage display. J Mol Biol 234:564-78

Matarese G, Moschos S, Mantzoros C S (2005) Leptin in immunology J Immunol 174:3137-42

Meilhoc E, Masson J M, Teissie J (1990) High efficiency transformation of intact yeast cells by electric field pulses. Biotechnology (N Y) 8:223-7

Niv-Spector L, Gonen-Berger D, Gourdou I, Biener E, Gussakovsky E E, Benomar Y, Ramanujan K V, Taouis M, Herman B, Callebaut I, Djiane J, Gertler A (2005) Identification of the hydrophobic strand in the A-B loop of leptin as major binding site III: implications for large-scale preparation of potent recombinant human and ovine leptin antagonists. Biochem J 391:221-30

Ozcan L, Ergin A S, Lu A, Chung J, Sarkar S, Nie D, Myers M G Jr, Ozcan U Endoplasmic reticulum stress plays a central role in development of leptin resistance. 2009 Cell Metab. 9:35-51.

Pearce K H, Jr., Cunningham B C, Fuh G, Teeri T, Wells J A (1999) Growth hormone binding affinity for its receptor surpasses the requirements for cellular activity. Biochemistry 38:81-9

Peelman F, Iserentant H, De Smet A S, Vandekerckhove J, Zabeau L, Tavernier J (2006) Mapping of binding site III in the leptin receptor and modeling of a hexameric leptin.leptin receptor complex. J Biol Chem 281:15496-504

Peelman F, Van Beneden K, Zabeau L, Iserentant H, Ulrichts P, Defeau D, Verhee A, Catteeuw D, Elewaut D, Tavernier J (2004) Mapping of the leptin binding sites and design of a leptin antagonist. J Biol Chem 279:41038-46

Peelman F, Iserentant H, Eyckerman S, Zabeau L, Tavernier J. (2005) Leptin, immune responses and autoimmune disease. Perspectives on the use of leptin antagonists. Curr Pharm Des. 11:539-48. Review.

Raver N, Gussakovsky E E, Keisler D H, Krishna R, Mistry J, Gertler A (2000) Preparation of recombinant bovine, porcine, and porcine W4R/R5K leptins and comparison of their activity and immunoreactivity with ovine, chicken, and human leptins. Protein Expr Purif 19:30-40

Raymond C K, Pownder T A, Sexson S L (1999) General method for plasmid construction using homologous recombination. Biotechniques 26:134-8, 140-1

Salomon G, Niv-Spector L, Gussakovsky E E, Gertler A (2006) Large-scale preparation of biologically active mouse and rat leptins and their L39A/D40A/F41A muteins which act as potent antagonists. Protein Expr Purif 47:128-36

Sandowski Y, Raver N, Gussakovsky E E, Shochat S, Dym 0, Livnah 0, Rubinstein M, Krishna R, Gertler A (2002) Subcloning, expression, purification, and characterization of recombinant human leptin-binding domain. J Biol Chem 277:46304-9

Somasundar P, Frankenberry K A, Skinner H, Vedula G, McFadden D W, Riggs D, Jackson B, Vangilder R, Hileman S M, Vona-Davis L C (2004) Prostate cancer cell proliferation is influenced by leptin. J Surg Res 118:71-82

Turek V F, Trevaskis J L, Levin B E, Dunn-Meynell A A, Irani B, Gu G, Wittmer C, Griffin P S, Vu C, Parkes D G, Roth J D (2010) Mechanisms of amylin/leptin synergy in rodent models. Endocrinology 151:143-52

Wang M Y, Chen L, Clark G O, Lee Y, Stevens R D, Ilkayeva O R, Wenner B R, Bain J R, Charron M J, Newgard C B, Unger R H. Leptin therapy in insulin-deficient type I diabetes. 2010 Proc. Natl. Acad. Sci. U.S.A. 107: 4813-9.

Zabeau L, Lavens D, Peelman F, Eyckerman S, Vandekerckhove J, Tavernier J. 2003 FEBS Lett. 546: 45-50

Zhang F, Basinski M B, Beals J M, Briggs S L, Churgay L M, Clawson D K, DiMarchi R D, Furman T C, Hale J E, Hsiung H M, Schoner B E, Smith D P, Zhang X Y, Wery J P, Schevitz R W (1997) Crystal structure of the obese protein leptin-E100. Nature 387:206-9

The invention claimed is:

1. A synthetic leptin antagonist comprising:
   (a) a full length modified mammalian leptin polypeptide in which:
      (i) the LDFI hydrophobic binding site at the position corresponding to positions 39-42 of the wild-type human leptin is modified such that from two to four amino acid residues of said hydrophobic binding site are substituted with different amino acid residues such that the site becomes less hydrophobic; and
      (ii) the aspartic acid at the position corresponding to position 23 of the wild-type human leptin (D23) is substituted with an amino acid residue selected from the group consisting of glycine, alanine, leucine, lysine, arginine, phenylalanine, tryptophan and histidine, or the threonine at the position corresponding to position 12 of the wild-type human leptin (T12) is substituted with a different amino acid residue that is hydrophobic; or
   (b) a pharmaceutically acceptable salt of (a).

2. The synthetic leptin antagonist of claim 1, wherein D23 is substituted with a hydrophobic amino acid selected from the group consisting of glycine, alanine, leucine and phyenylalanine, or a positively charged amino acid residue selected from the group consisting of lysine and arginine.

3. The synthetic leptin antagonist according to claim 2, wherein further amino acid residues are substituted as follows:
   (a) the leucine at the position corresponding to position 68 of the wild-type human leptin (L68) is substituted with methionine, the serine at the position corresponding to position 97 of the wild-type human leptin (S97) is substituted with phenylalanine and the serine at the position corresponding to position 132 of the wild-type human leptin (S132) is substituted with tyrosine;
   (b) the glycine at the position corresponding to position 112 of the wild-type human leptin (G112) is substituted with serine; or
   (c) the threonine at the position corresponding to position 37 of the wild-type human leptin (T37) is substituted with alanine and the glycine at the position corresponding to position 44 of the wild-type human leptin (G44) is substituted with aspartic acid.

4. The synthetic leptin antagonist according to claim 1 in pegylated form.

5. An isolated DNA molecule encoding a synthetic leptin antagonist of claim 1.

6. A pharmaceutical composition comprising a synthetic leptin antagonist according to claim 1, and a pharmaceutically acceptable carrier.

7. The pharmaceutical composition according to claim 6, comprising the synthetic leptin antagonist in a pegylated form.

8. A method for treatment of a disease or condition selected from the group consisting of metabolic syndrome, non-alcoholic steatohepatitis, atherosclerosis, type II diabetes, anorexia, cachexia, cancer, and auto-inflammatory and autoimmune diseases, comprising administering to a patient in need an effective amount of the synthetic leptin antagonist of claim 1, wherein said synthetic leptin antagonist is optionally in pegylated form.

9. The method of claim 8, wherein the auto-inflammatory and autoimmune diseases are selected from the group consisting of multiple sclerosis, inflammatory bowel syndrome and rheumatoid arthritis.

10. A synthetic leptin antagonist consisting of a polypeptide having the amino acid sequence of SEQ ID NO: 1, optionally in pegylated form, or a pharmaceutically acceptable salt thereof.

11. An isolated DNA molecule encoding a synthetic leptin antagonist of claim 10.

12. The isolated DNA molecule according to claim 11, having the DNA sequence of SEQ ID NO: 4.

13. A pharmaceutical composition comprising a synthetic leptin antagonist according to claim 10, and a pharmaceutically acceptable carrier.

14. A method for treatment of a disease or condition selected from the group consisting of metabolic syndrome, non-alcoholic steatohepatitis, atherosclerosis, type II diabetes, anorexia, cachexia, cancer, and auto-inflammatory and autoimmune diseases, comprising administering to a patient in need an effective amount of the synthetic leptin antagonist of claim 10.

15. The method of claim 14, wherein the auto-inflammatory and autoimmune diseases are selected from the group consisting of multiple sclerosis, inflammatory bowel syndrome and rheumatoid arthritis.

* * * * *